US008030016B2

(12) United States Patent
Ochiai et al.

(10) Patent No.: US 8,030,016 B2
(45) Date of Patent: Oct. 4, 2011

(54) METHOD FOR SCREENING FOR VITAMIN D RECEPTOR LIGANDS

(75) Inventors: Eiji Ochiai, Tokyo (JP); Kazuyoshi Yamaoka, Tokyo (JP); Ken-ichiro Takagi, Tokyo (JP); Yu Tsushima, Tokyo (JP); Shigeaki Kato, Tokyo (JP); Hirochika Kitagawa, Tokyo (JP); Ichiro Takada, Tokyo (JP)

(73) Assignees: Teijin Pharma Limited, Tokyo (JP); The University of Tokyo, Tokyo (JP)

( * ) Notice: Subject to any disclaimer, the term of this patent is extended or adjusted under 35 U.S.C. 154(b) by 0 days.

(21) Appl. No.: 12/375,843

(22) PCT Filed: Jul. 30, 2007

(86) PCT No.: PCT/JP2007/065310
§ 371 (c)(1),
(2), (4) Date: Jun. 15, 2009

(87) PCT Pub. No.: WO2008/016155
PCT Pub. Date: Feb. 7, 2008

(65) Prior Publication Data
US 2010/0068707 A1 Mar. 18, 2010

(30) Foreign Application Priority Data
Jul. 31, 2006 (JP) ................................. 2006-208620

(51) Int. Cl.
*G01N 33/53* (2006.01)
*A01N 1/02* (2006.01)
*C12N 15/00* (2006.01)
*C07H 21/04* (2006.01)

(52) U.S. Cl. .............. 435/7.8; 435/2; 435/7.1; 435/810; 435/320.1; 536/23.4

(58) Field of Classification Search .................. None
See application file for complete search history.

(56) References Cited

U.S. PATENT DOCUMENTS
5,578,708 A * 11/1996 Okazaki et al. ............... 530/399
2005/0042730 A1 * 2/2005 Kato et al. ..................... 435/69.1

FOREIGN PATENT DOCUMENTS
WO 00/15836 A2 3/2000
WO 2004/045371 6/2004

OTHER PUBLICATIONS

Y. Ma, et al., "Identification and characterization of noncalcemic, tissue-selective, nonsecosteroidal vitamin D receptor modulators," Journal of Clinical Investigation, 2006, pp. 892-904, vol. 116, No. 4.
M.F. Van Gurp, et al., "The CCAAT displacement protein/cut homeodomain protein represses osteocalcin gene transcription and forms complexes with the retinoblastoma protein-related protein p107 and cyclin A," Cancer Research, 1999, pahes 5980-5988, vol. 59.

A. Nepveu, "Role of the multifunctional CDP/Cut/Cux homeodomain transcription factor in regulating differentiation, cell growth and development," Gene, 2001, pp. 1-15, vol. 270. No. 1-2.
S. Nagpal, et al., "Noncalcemic actions of vitamin D receptor ligands," Endocrine Reviews, 2005, pp. 662-687, vol. 26, No. 5.
European Search Report dated Jan. 29, 2010, as issued in European Application No. 07791983.5.
Shalnik, et al., "CCAAT displacement protein as a repressor of the myelomonocytic-specific gp91-phox gene promoter", The Journal of Biological Chemistry, vol. 266, No. 25, pp. 16736-16744, 1991.
Balint, et al., "Phenotype discovery by gene expression profiling: Mapping of biological processes linked to BMP-2-mediated osteoblast differentiation", Journal of Cellular Biochemistry, Wiley-Liss, Inc., vol. 89, No. 2, pp. 401-426, May 15, 2003.
Ochiai, et al., "Identification of osteoblast-specific co-regulator complex for vitamin D receptor (VDR)", Journal of Bone and Mineral Research, American Society for Bone and Mineral Research, vol. 21, No. Suppl. 1, p. S460, Sep. 1, 2006.
Matsumoto et al., Stimulation by 1, 25-Dihydroxy $D_3$ of in Vitro Mineralization Induced by Osteoblast-like MC3T3-E1 Cells, Bone vol. 12, 27-32, (1991).
Oda A. et al., Two Distinct Coactivators, DRIP/Mediator and SRC/p 160, Are Differentially Involved in Vitamin D Receptor Transactivation during Keratinocyte Differentiation, Mol. Endocrinol, vol. 17, 2329-2339 (2003).
Neufeld E. J. et al., Human CCAAT displacement protein is homologous to the Drosophila homeoprotein, cut, (1992), Nature. Genet. 1. 50-55.
Andres. V. et al., *Clox*, a mammalian homeobox gene relates to *Drosophila cut*, encodes DNA-binding regulatory proteins differentially expressed during development, (1992) Development. 116, 321-334.
Valarche I et al., The mouse homeodomain protein Phox2 regulates *Ncam* promoter activity in concert with Cux/CDP and is a putative determinant of neurotransmitter phenotype, (1993) Development 119, 881-896. Yoon S.O. et al., Isolation of Two E-box Binding Factors That Interact with the Rat Tyrosine Hydroxylase Enhancer, (1994) J. Biol. Chem., 269, 18453-18462.
Alain Nepveu, Role of the multifunctional CDP/Cut/Cux homeodomain transcription factor in regulating differentiation, cell growth and development, (2001), Gene 270: 1-15.
Jack et al., Expression of the cut locus in the Drosophila wing margin is required for cell type specification and is regulated by a distant enhancer, (1991), Development, 113:735-747.
Ellis et al., The transcriptional repressor CDP(Cut1) is essential for epithelial cell differentiation of the lung and the hair follicle, Genes & Development, 15:2307-2319, (2001).
Ledford et al., Deregulated Expression of the Homeobox Gene Cux-1 in Transgenic Mice Results in Downregulation of $p27^{kip1}$ Expression during Nephrogenesis, Glomerular Abnormalities, and Multiorgan Hyperplasia, (2002), Developmental Biology, 245:157-171.
Holthuis et al. Tumor Cells Exhibit Deregulation of the Cell Cycle Histone Gene Promoter Factor HiNF-D, (1990), Science, 247:1454-1457.

(Continued)

*Primary Examiner* — Shulamith H Shafer
(74) *Attorney, Agent, or Firm* — Sughrue Mion, PLLC

(57) ABSTRACT

The present invention relates to a screening method for a compound and includes a step of detecting binding between a vitamin D receptor and CDP. A novel method enabling screening in vitro of a compound having strong bone forming action and low side effects, a compound participating in osteoblast differentiation and selected by the method of screening, a therapeutic agent containing the compound for diseases intervening in the increase in vitamin D-mediated transcriptional activity by a complex of a vitamin D receptor and CDP, and a kit for performing the screening method are provided.

15 Claims, 12 Drawing Sheets

OTHER PUBLICATIONS

Pattison et al., CCAAT Displacement Protein, a Regulator of Differentiation-Specific Gene Expression, Binds a Negative Regulatory element within the 5' End of the Human Papillomavirus Type 6 Long Control Region, (1997) Journal of Virology, vol. 71, No. 3, 2013-2022.

Liu et al. The Matrix Attachment Region-Binding Protein SATB1 Participates in Negative Regulation of Tissue-Specific Gene Expression, (1997), Molecular and Cellular, Biology, vol. 17, No. 9, 5275-5287.

Burglin et al. Loss and gain of domains during evolution of cut superclass homeobox genes, (2002), Int. J. Dev. Biol., 46:115-123.

Dickinson et al., An Atypical Homeodomain in SATB1 Promotes Specific Recognition of the key Structural Element in a Matrix Attachment Region, (1997), Journal of Biological Chemistry, vol. 272, No. 17, 11463-11470.

Moon et al., CCAAT Displacement Activity Involves CUT Repeats 1 and 2, Not the CUT Homeodomain, (2000), Journal of Biological Chemistry, vol. 275, No. 40, 31325-31334.

Moon et al., S Phase-Specific Proteolytic Cleavage Is Required to Activate Stable DNA Binding by the CDP/ Cut Homeodomain Protein, (2001) Molecular and Cellular Biology, vol. 21, No. 18, 6332-6345.

Wang et al., Cux/CDP Homeoprotein Is a Component of NF-µNR and Represses the Immunoglobulin Heavy Chain Intronic Enhancer by Antagonizing the Bright Transcription Activator, (1999) Molecular and Cellular Biology, vol. 19, No. 1, 284-295.

\* cited by examiner

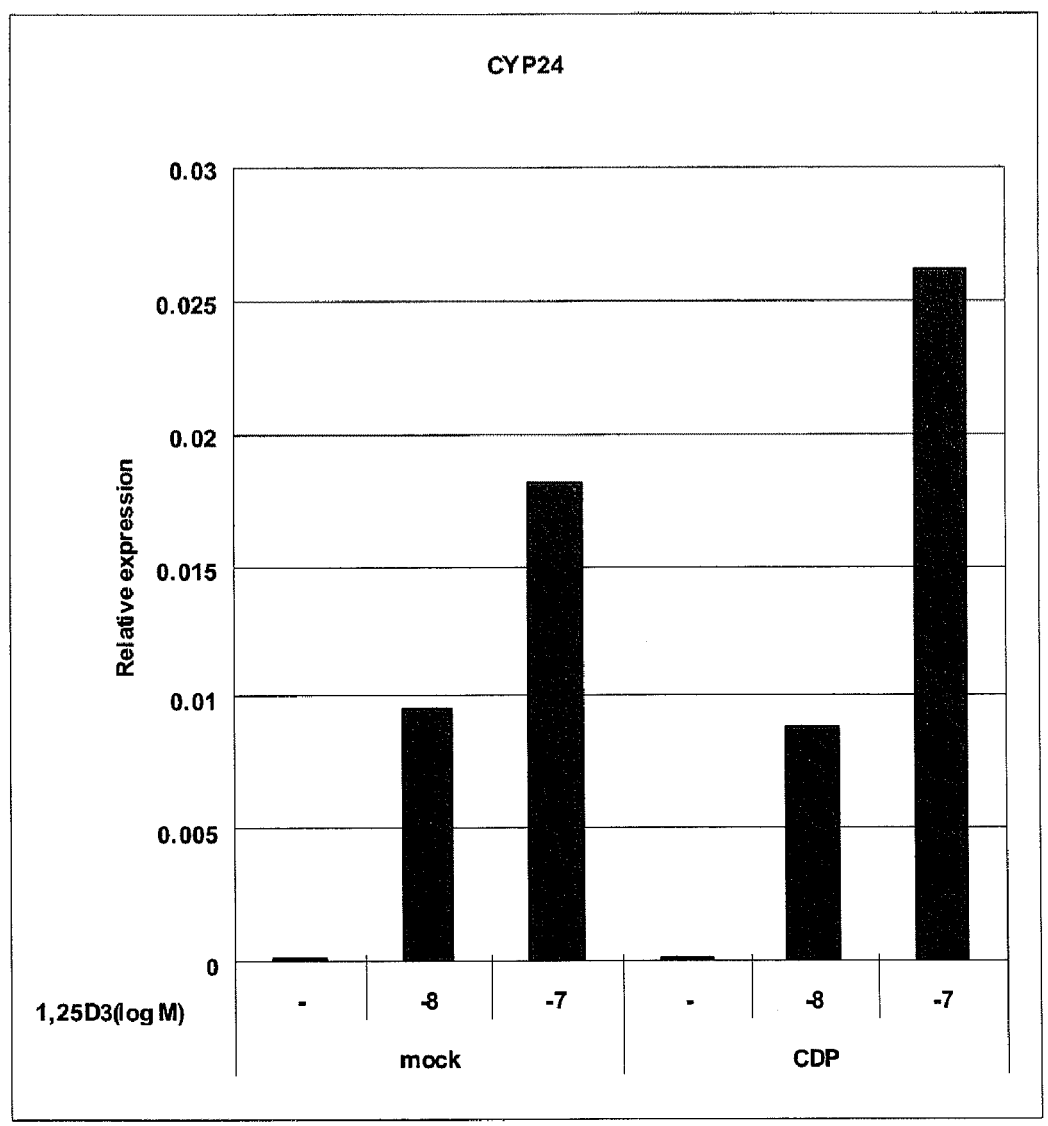

```
                              SEQUENCE LISTING

<160> NUMBER OF SEQ ID NOS: 5

<210> SEQ ID NO 1
<211> LENGTH: 17
<212> TYPE: DNA
<213> ORGANISM: Homo sapiens

<400> SEQUENCE: 1
gcaggtcagc gagggcg                                                      17

<210> SEQ ID NO 2
<211> LENGTH: 17
<212> TYPE: DNA
<213> ORGANISM: Homo sapiens

<400> SEQUENCE: 2
ggagttcacc gggtgtg                                                      17

<210> SEQ ID NO 3
<211> LENGTH: 17
<212> TYPE: DNA
<213> ORGANISM: Homo sapiens

<400> SEQUENCE: 3
ccgggtgaac gggggca                                                      17

<210> SEQ ID NO 4
<211> LENGTH: 20
<212> TYPE: DNA
<213> ORGANISM: Homo sapiens

<400> SEQUENCE: 4
tttggtgact caccgggtga                                                   20

<210> SEQ ID NO 5
<211> LENGTH: 29
<212> TYPE: DNA
<213> ORGANISM: Homo sapiens

<400> SEQUENCE: 5
tttggtgact caccgggtga acgggggca                                         29
```

METHOD FOR SCREENING FOR VITAMIN D RECEPTOR LIGANDS

TECHNICAL FIELD

The present invention relates to a novel method of screening for compounds participating in osteoblast differentiation. In particular, the present invention relates to an in vitro use of VDR (vitamin D receptor) and CDP (CCAAT Displacement Protein) to screen for the above compounds.

BACKGROUND ART

Active vitamin $D_3$ derivatives such as $1\alpha,25$-dihydroxyvitamin $D_3$ (hereafter "1,25 $(OH)_2D_3$ or 1,25D3) or $1\alpha$-hydroxy vitamin $D_3$ (hereafter "$1\alpha$ (OH)D3) have extensive clinical applications as therapeutic substances for metabolic bone diseases such as osteoporosis. The physiological effect of these active vitamin $D_3$ derivatives is known to be mediated by VDR. VDR is not only present in tissue such as the small intestine, bone, kidneys and parathyroid but is also present in various types of cells including immune system cells and tumor cells. Consequently active vitamin $D_3$ derivatives are known to have various physiological effects including (1) calcium and bone metabolism regulation, (2) proliferation inhibition of tumor cells, epidermal cells and epithelial cells, and (3) regulation of immune system cells.

Animal experiments using active vitamin $D_3$ derivatives such as 1,25 $(OH)_2D_3$ or $1\alpha$ (OH)D3 have demonstrated relatively potent effects in increasing bone mass depending on the experimental conditions. On the other hand, in a clinical environment, the effect of increasing the bone density of the lumbar vertebrae or the collum femoris is poor. When using the bone density as a standard, although groups receiving doses of active vitamin $D_3$ derivatives (clinical dosage) display superior results to groups only receiving dosages of calcium, the bone mass increase action is weaker than groups receiving administration of bisphosphonates. However, clinical results have been reported showing efficacy in suppressing fractures greater than that expected from the bone mass. The pharmacological effects described above have resulted in long-standing use as a therapeutic substance for osteoporosis. However, the mechanism for bone mass increase mediated by administration of active vitamin $D_3$ derivatives remains unclear.

Active vitamin $D_3$ derivatives in vitro are known to promote differentiation of osteoblasts participating in osteogenesis. However, a molecular biological mechanism of this action remains unclear.

1,25 $(OH)_2D_3$ is known to induce genetic expression of known osteoblast differentiation markers such as osteopontin and osteocalcin in bone tissue which is one of the target tissues. Osteoblasts in cell culture systems are known to differentiate as a result of 1,25 $(OH)_2D_3$ action (Non-patent Document 1). Furthermore the action of 1,25 $(OH)_2D_3$ in other target organs such as the intestines or the kidneys has long been known to induce the genes for calcium binding protein (calbindin) which participates in calcium uptake rather than to induce the genetic expression of osteoblast markers. Thus, the action depends on the type of tissue. As a result, since vitamin $D_3$ derivatives increase blood levels of calcium, side effects such as hypercalcemia constitute problems for their clinical application. Therefore, screening for compounds lacking in, or having weak calcium blood level increase action could lead to the development of superior therapeutic substances for metabolic bone diseases with few side effects.

VDR-mediated transcriptional activity is generally known to occur through the participation of transcription co-factor (co-activator/co-repressor) in addition to VDR and the basic transcription factor. Although several transcription cofactors displaying VDR binding activity have been identified, a cofactor which may explain the role of 1,25 $(OH)_2D_3$ in the mechanism of osteoblast differentiation remains elusive. The existence of such tissue-specific genetic expression control suggests that expression or recruitment of VDR-related cofactors may depend on the tissue type. For example, differences have recently been reported in the complexes forming VDR before and after keratinocyte differentiation (Non-patent Document 2). These results suggest that cellular specificity or tissues having various intracellular genetic expression mechanisms regulated by VDR may depend on differences in the complexes forming VDR. However, identification or isolation of complexes forming VDR in osteoblasts has not been reported.

Turning now to CDP, mammalian homologues of Cut homeodomain proteins in yellow fruit flies have been isolated from mammals such as humans (Non-patent Document 3), dogs (Non-patent Document 4), mice (Non-patent Document 5) and rats (Non-patent Document 6). These homologues are respectively referred to as CDP (CCAAT Displacement Protein), Clox (Cut-like homeobox), Cux-1 (Cut homeobox) and CDP-2. Human CDP is referred to as both CUT-LIKE 1:CUTL1.

CDP belongs to a family of transcription factors present in higher order eukaryotes and is related to the control of cellular differentiation and proliferation (Non-patent Document 7). Numerous phenotypic variations in yellow fruit flies have been reported to result from insertion of a transposable insulator sequence (insulator sequence) interfering with the tissue-specific enhancer function of Cut which is a CDP yellow fruit fly homologue (Non-patent Document 8). Such phenotypes are known to be expressed in several structures in the wings (cut wings), legs, external sensory organs, Malpighian renal tubules, tracheal system or central nervous system (Non-patent Document 9). Similar to the Cux-1 and Cux-2 genes existing in mice and chickens, humans have two CDP/Cux genes: CDP-1 and CDP-2 (Non-patent Document 10). Although Cux-2 shows initial expression in nerve tissue, Cux-1 is present in almost all tissue types (Non-patent Document 10). A Cux-1 knockout mouse displays phenotypes expressed in various organs including curly whiskers, growth retardation, delayed differentiation of lung epithelia, altered hair follicle morphogenesis, male infertility, and T and B cell deficit (Non-patent Document 11). In comparison to small Cux-1 knockout mice, a genetically recombinant mouse expressing Cux-1 displays multiple organ hyperplasia and organ hypertrophy under control of the CMV enhancer/promoter. (Non-patent Document 12). In this manner, genetic experiments using yellow fruit fly and mice have shown the important role of CDP/Cux/Cut genes in the homeostasis and development of various tissues.

Expression and activation of CDP in tissue culture systems are related to cell proliferation (Non-patent Document 13), suppress CDP genetic expression occurring in terminally differentiated cells (Non-patent Document 14) and participate in the modification of matrix attachment regions (Non-patent Document 15). CDP/Cux/Cut proteins have respective DNA binding domains. All proteins contain at least one Cut homeodomain (HD) and three Cut repeats (CR1, CR2 and CR3). The cut superclass of the homeobox genes is divided into three classes: CUX, ONECUT and SATB (Non-patent Document 16). The yellow fruit fly Cut, human CDP and mouse Cux genes contain three Cut repeats and a ONECUT gene containing one Cut repeat is present in each type (Non-patent Document 10). SATB1 contains two Cut repeat-like domains and an atypical Cut-like homeodomain (Non-patent Document 17).

Although the individual Cut repeats themselves do not bind to DNA, DNA-binding affinity is enabled via certain combinations of Cut repeats or the Cut homeodomain (Non-patent Document 18). There have been two reports of intracellular DNA binding activity by CDP/Cux. CDP/Cux p200 transiently binds to DNA in the same manner as CR1CR2 and displays CCAAT substitution activity (Non-patent Document 10). In the G1/S transition of the cell cycle, proteolytic processing of the decomposable p200 protein produces CDP/Cux p110. CDP/Cux p110 contains CR2CR3HD which displays different DNA binding specificity and kinetics (Non-patent Document 19). In particular, p110 can form stable interactions with DNA. High levels of p110 isoforms are expressed in uterine leiomyomas (Non-patent Document 20).

Patent Document 1 discloses the discovery that p'75, a novel isoform of CDP/Cux, is encoded by mRNA initiated by intron 20 in the CDP/Cux site. This novel isoform displays distinct DNA binding activity to p200, p110 and p100 CDP/Cux isoforms. Although mRNA expression initiated in intron 20 is limited to certain tissue or cell types, the expression is activated in mammary tumor cell strains, primary human mammary tumors and other cancerous tissues. Consequently, antibodies against isoforms (CDP/Cux) of truncated CCAAT-substituted proteins/Cut homeobox find useful application in methods of diagnosis and prognosis for the detection of cancer. Furthermore, a method of detecting cancer by detecting RNA transcripts encoding p75 is disclosed. Moreover, CDP/Cux are known to suppress enhancer activity by competitively binding with the transcription factor binding at the matrix attachment regions of the intron enhancer (Eμ) of the immunoglobin heavy chain in a cell type specific manner or differentiation stage specific manner (Non-patent Document 21).

However these reports have no clear relationship to CDP function with respect to bone or vitamin D receptors.

Patent Document 1: International Publication No. 2004/045371 Pamphlet
Non-patent Document 1: Matsumoto et al., Bone Vol. 12, 27-32, (1991)
Non-patent Document 2: Oda A. et al., Mol. Endocrinol. Vol. 17, 2329-2339, (2003)
Non-patent Document 3: Neufeld, E. J. et al., (1992) Nat. Genet. 1, 50-55
Non-patent Document 4: Andres, V. et al., (1992) Development, 116, 321-334
Non-patent Document 5: Valarche, I. et al., (1993) Development, 119, 881-896
Non-patent Document 6: Yoon, S. O. et al., (1994) J. Biol. Chem. 269, 18453-18462
Non-patent Document 7: Nepveu (2001) Gene 270:1-15
Non-patent Document 8: Jack, et al., (1991) Development 113: 735-747
Non-patent Document 9: Jack, et al., (1991) supra
Non-patent Document 10: Neufeld, E. J., et al., (1992) supra
Non-patent Document 11: Ellis, et al., (2001) supra
Non-patent Document 12: Ledford, et al., (2002) Dev. Biol. 245: 157-171
Non-patent Document 13: Holthuis, et al., (1990) Science 247: 1454-1457
Non-patent Document 14: Pattison, et al., (1997) J. Virol. 71: 2013-2022
Non-patent Document 15: Liu, et al., (1997) Mol. Cell. Biol. 17:5275-5287
Non-patent Document 16: Burglin and Cassata (2002) Int. J. Dev. Biol. 46:115-123
Non-patent Document 17: Dickinson, et al. (1997) J. Biol. Chem. 272: 11463-11470
Non-patent Document 18: Moon, et al., (2000) J. Biol. Chem. 275: 31325-31334
Non-patent Document 19: Moon, et al., (2001) Mol. Cell. Biol. 21: 6332-6345
Non-patent Document 20: Moon, et al., (2001) supra
Non-patent Document 21: Wang, et al., (1999) MOLECULAR AND CELLULAR BIOLOGY, 19:284-295

DISCLOSURE OF THE INVENTION

Problems to be Solved by the Invention

As described above, when preparing active vitamin $D_3$ derivatives for clinical use, there is a need for a novel method of screening for derivatives which are either lacking in, or have weak side effects such as hypercalcemia. Determination of whether or not a derivative has potent osteogenetic action together with low side effects requires long-term examination of the extent of osteogenetic action and any side effects such as hypercalcemia by actual administration of the derivative to an animal subject and could not be examined simply by use of cell evaluation systems. Therefore, one object of the present invention is to provide a novel method allowing for the in vitro screening of active vitamin $D_3$ derivatives having potent osteogenetic action together with low side effects.

Means to Solve the Problems

The present inventors realized that HOS-TE85 cells differentiate during culturing in the presence of 1,25 $(OH)_2D_3$, but that this type of action was not seen in cells other than osteoblasts such as HeLa cells which are uterine cancer cells or MCF-7 cells which are mammary cancer cells. In that context, while searching for complexes forming VDR in HOS-TE85 cells, CDP displaying ligand-dependent direct binding to VDR was identified. Conspicuous levels of ligand-dependent binding between VDR and CDP were observed in osteoblasts having abundant CDP. The present inventors have realized that 1,25 $(OH)_2D_3$ dependent transcriptional activity is increased by VDR causing an over-expression of CDP and that CDP increases 1,25 $(OH)_2D_3$ dependent transcriptional activity.

In one aspect of a screening method of the present invention, the action of compounds in relation to binding between VDR and CDP is used as an indicator.

In other words, the present invention relates to a method of screening compounds having a binding action including a step of detecting the presence or absence of binding between VDR and CDP in the presence of a test compound.

The compound may be a compound having affinity for VDR and/or CDP.

The method of screening can be performed using a cell producing both VDR and CDP or a cellular preparation of such a cell. Alternatively, at least one of VDR and CDP may be used in a purified form.

The cell producing both VDR and CDP may be an osteoblast-like cell or may be a cell containing and expressing at least one of a VDR gene and a CDP gene.

Further, the present invention relates to a method of screening a compound which increases the transcriptional activity by a complex of VDR and CDP, wherein the method includes the step of detecting an increase in the transcriptional activity by a complex of a VDR and CDP due to the presence of the test compound.

The compound may be a compound having affinity for VDR and/or CDP.

The step of detecting an increase in transcriptional activity by a complex of VDR and CDP can be performed by detecting a further increase in VDR-mediated transcriptional activity by over-expressing CDP, or by detecting a further increase in CDP-mediated transcriptional activity by over-expressing VDR.

An increase in the transcriptional activity by a complex of VDR and CDP can be detected in a cell expressing and/or producing both of VDR and CDP.

A cell expressing and/or producing both of VDR and CDP may be an osteoblast-like cell.

A cell expressing and/or producing both of VDR and CDP may contain at least one of a VDR gene and a CDP gene.

The method of screening can measure an increase in CDP or VDR-mediated transcriptional activity using a reporter gene assay system.

The increase in transcriptional activity by the complex of VDR and CDP is measured using expression of an osteoblast differentiation marker gene or a VDR target gene as an indicator. The VDR target gene may be a CYP24 gene and the osteoblast differentiation marker gene is selected from an osteocalcin gene and an alkali phosphatase gene.

A vitamin D derivative is an example of a candidate compound identified by the screening method of the present invention.

A compound identified by the screening method of the present invention can be used as a compound inducing osteoblast differentiation or a compound displaying bone mass increasing action in animals.

The present invention further relates to a compound selected by the screening method above.

A vitamin D derivative is an example of such a compound.

The present invention relates to a therapeutic substance containing the above compound for diseases wherein the substance has an effect of increasing bone mass or a disease wherein the substance has an effect of promoting osteoblast differentiation, or a disease wherein the substance increases in VDR-mediated transcriptional activity by a complex of VDR and CDP.

The disease includes a metabolic bone disease.

The metabolic bone disease may for example be osteoporosis.

The present invention relates to a kit for performing the screening method comprising at least one of (a) a vector comprising a VDR recognition sequence and a reporter gene for evaluating an increase in VDR-mediated transcriptional activity; and (b) a vector comprising a CDP recognition sequence and a reporter gene for evaluating an increase in CDP-mediated transcriptional activity; and (c) a reagent for detecting a product of the reporter gene.

The present invention relates to a kit for performing the screening method, comprising (a) a vector comprising a VDR recognition sequence, a CDP recognition sequence, and a reporter gene for evaluating an increase in transcriptional activity by a complex of VDR and CDP; and (b) a reagent for detecting a product of the reporter gene.

BRIEF DESCRIPTION OF THE DRAWINGS

In FIG. 5A, ◇ denotes the vehicle, ● is $10^{-7}$ M 1,25 $(OH)_2D_3$, ▲ is $10^{-8}$ M 1,25 $(OH)_2D_3$ and ■ isle M 1,25 $(OH)_2D_3$.

In FIG. 5B, ◇ denotes the vehicle, ● is $10^{-7}$ M 1,25 $(OH)_2D_3$, ▲ is $10^{-8}$ M 1,25 $(OH)_2D_3$ and ■ is $10^{-9}$ M 1,25 $(OH)_2D_3$.

FIG. 7A shows the level of expression of the CYP24 gene in cultured cells when HOS cells containing pSPORT6-CDP are cultured in the presence of 1,25 $(OH)_2D_3$ at various concentrations. In FIG. 7A, "mock" denotes HOS cells not containing pSPORT6-CDP and "CDP" denotes HOS cells containing pSPORT6-CDP.

In FIG. 7B, "mock" denotes HOS cells not containing pSPORT6-CDP and "CDP" denotes HOS cells containing pSPORT6-CDP.

In FIG. 7C, "mock" denotes HOS cells not containing pSPORT6-CDP and "CDP" denotes HOS cells containing pSPORT6-CDP.

BEST MODE FOR CARRYING OUT THE INVENTION

Figure 1:
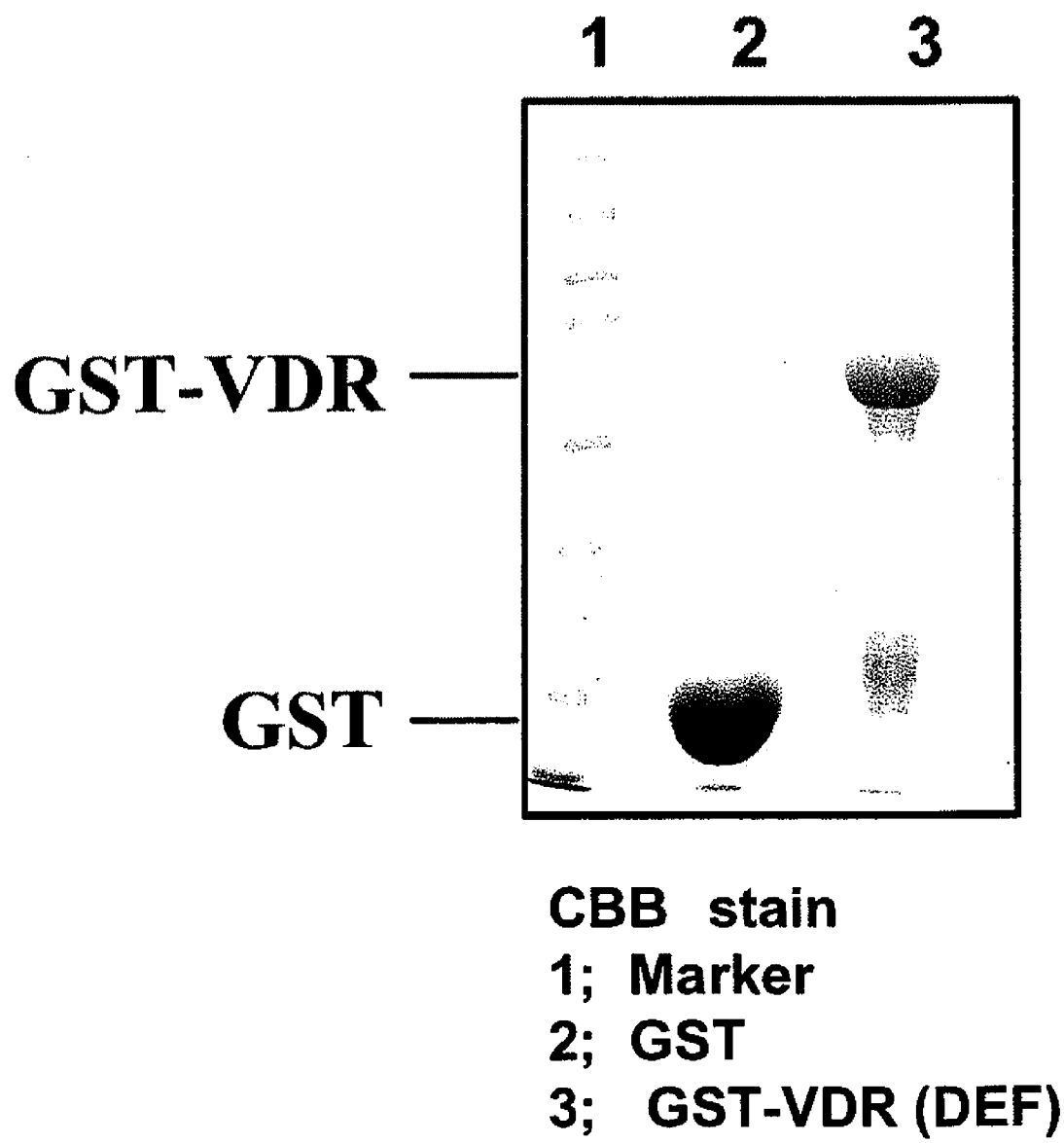
FIG. 1 depicts an SDS-PAGE image of GST resin and GST-VDR (DEF) resin.

The present invention relates to a method of screening compounds having binding action to VDR and CDP, the method comprising the step of detecting binding between VDR and CDP resulting from the presence of a test compound. The present invention is based on the insight that VDR and CDP display VDR ligand dependent binding.

Since VDR and CDP display VDR ligand dependent binding, one form of a compound selected using the screening system of the present invention is a VDR ligand. Since an object of the screening method of the present invention is the identification of a compound which increases the quantitative or kinetic binding between VDR and CDP, a compound displaying affinity for VDR and/or CDP is an example of compound screened by the screening method of the present invention. In the present specification, a compound having affinity to VDR and/or CDP refers to VDR ligands, CDP ligands, a compound increasing binding between VDR and CDP, or a compound increasing transcriptional activity by a complex of VDR and CDP. For example, vitamin D derivatives are candidate compounds for such compounds. A vitamin D derivative as used herein refers to a steroid displaying the biological action of an ergocalciferol or cholecalciferol. The invention is not limited to vitamin D derivates as long as a compound satisfies the object of the method of screening according to the present invention to isolate compounds increasing the quantitative or kinetic binding between VDR and CDP or a compound increasing transcriptional activity by a complex of VDR and CDP.

In the present invention, VDR refers to a nuclear protein of mammalian origin which displays binding activity to 1,25 (OH)$_2$D$_3$. VDR of this type is preferably human, mouse or rat VDR, or more preferably human VDR. For information regarding the amino acid sequences of these forms of VDR, reference may be made to the disclosures regarding human: Swissprot Accession No. P11473, mouse: Swissprot Accession No. P48281, and rat: Swissprot Accession No. P13053. The VDR used in the present invention has a sequence containing the vitamin D binding region of at least the VDR amino acid sequence and is deficient for example in DNA binding regions. In the above VDR examples, the human VDR amino acid sequence disclosed in Swissprot Accession No. P11473 comprises at least a sequence containing an amino acid sequence from amino acid number 232 from the N-terminal to amino acid number 394 and has a bond to 1,25 (OH)$_2$D$_3$. VDR of the present invention includes fusion proteins between proteins and peptides having functions other than those of the VDR as described above. Examples of these substances include fusion proteins between VDR and glutathione-S-transferase (GST), GAL4-DNA binding domain protein, VP16 transcription active domain protein or fluorescent protein.

CDP (CCAAT Displacement Protein) is a protein which is reported for the first time in the present invention to display ligand-dependent direct binding to VDR in osteoblasts. This action is not seen in cells other than osteoblasts such as HeLa cells which are uterine cancer cells or MCF-7 cells which are mammary cancer cells. Furthermore, the present invention discloses the insight that the CDP is abundant in osteoblasts. CDP as referred to in this invention is a mammalian nuclear protein similar to the Cut gene in yellow fruit flies and is termed CUTL1, CUX, CASP, COY1 and Clox. CDP as referred to in the present invention is preferably CDP of human, mouse or rat origin and more preferably is of human origin. For information regarding the amino acid sequences of these forms of CDP, reference may be made to the disclosures of human: Swissprot Accession No. P39880, mouse: Swissprot Accession No. P53564, and rat: NCBI REFSEQ Accession No. XP_001070482. CDP as referred to in the present invention also includes known isoforms of CDP or proteins in which the substitution, deletion or insertion of an amino acid have been performed at a section of the CDP sequence, when these proteins have the function of increasing transcriptional activity by forming a bond to VDR or a complex with VDR in the presence of a VDR ligand. The CDP of the present invention further includes fusion proteins of proteins and peptides having functions other than the CDP as described above. Examples of these substances include fusion proteins of VDR with glutathione-S-transferase (GST), GAL4-DNA binding domain protein, VP16 transcription active domain protein or fluorescent protein.

Although the combination of VDR and CDP used in the method of screening according to the present invention may be composed of sequences of different origin, it is preferred that the combination of VDR and CDP is composed of sequences of the same origin and it is further preferred that the combination originates in VDR and CDP sequences of human origin.

The VDR ligand binding VDR and CDP increases expression of the osteocalcin gene and the alkali phosphatase gene which are markers for osteoblast differentiation. Consequently, the screening method of the present invention enables the identification of VDR ligands and other compounds participating in osteoblast differentiation. Furthermore, since such compounds participate in binding between VDR and CDP which are abundant in osteoblasts, the screening method of the present invention can identify compounds which select osteoblasts with low levels of side effects such as hypercalcemia.

The screening method of the present invention can be performed using cells producing both VDR and CDP or a cellular preparation of such cells. In other words, a test compound may be brought into direct contact with cells by culturing cells in the presence of the test compound or by mixing the test compound into a culture of the cells. Alternatively the cells may be prepared and the test compound may be mixed into a cellular preparation such as a lysate. In this manner, the screening method of the present invention can be performed in vitro using a cellular evaluation system comprising cells, or using a cell-free evaluation system such as a cell preparation.

The cellular preparation of cells may be suitably prepared by a person skilled in the art. Examples of a cellular preparation used in the screening method of the present invention include nuclear protein extract or a liquid cellular solution. Since cytoplasmic protein are contaminating proteins when purifying VDR-bound protein in the presence of ligands, nuclear protein extracts are particularly preferred for use in the cellular preparations used in the screening method of the present invention since they reduce the amount of protein from the cytoplasm which causes noise in the screening process.

Osteoblast-like cells are an example of cells producing both VDR and CDP which can be used in the screening method of the present invention. Osteoblast-like cells as used herein refer to, in addition to osteoblasts, cells expressing one or more general osteoblast markers. Osteoblast markers include alkali phosphatase, osteocalcin and bone sialoprotein and furthermore includes cells expressing the osteoblast markers in response to processes inducing differentiation into osteoblasts such as active vitamin D3, parathyroid hormone (PTH), ascorbic acid, co-stimulatory effects of ascorbic acid and beta-glycerophosphoric acid, and bone morphogenetic protein (BMP). Examples of these cells include primary human osteoblasts, osteoblasts, osteoblast-like cells from the periosteum, osteosarcoma cells, human stem cells and bone marrow mesenchymal cells. Commercially available cell lines include HOS cells (ATCC No. L-1543), SaM-1 cells, Saos-2 (ATCC No. HTB-85), U-20S cells (ATCC No. HTB-96), MG-63 cells (ATCC No. CRL-1427), MC3T3-E1 cells (ATCC No. CRL-2593), C3H/10T1/2 cells (ATCC No. CCL-226), UMR-106 cells (ATCC No. CRL-1661), ST2 cells (The Institute of Physical and Chemical Research, Tsukuba Institute, Bioresource Center, Cell No. RCB0224) and ROS17/2.8 (The Institute of Physical and Chemical Research, Tsukuba Institute, Bioresource Center, Cell No. RCB462). However the invention is not limited to these examples. Since the cells used in screening according to the present invention may be cells producing both VDR and CDP, cells into which VDR genes or CDP genes have been introduced may also be used.

The VDR genes may be introduced as appropriate selected by a person skilled in the art. The method of introducing genes includes lipofection, calcium phosphate methods, DEAF dextran methods or electroporation methods. Host cells for the introduction of genes may be suitably selected by a person skilled in the art. Suitable host cells include, for example, HOS cells, SaM-1 cells, jurkat cells, HeLa cells, MCF-7 cells, HepG2, CaCO-2, Saos-2, K562, CV-1, COS-1, COS-7, NIH3T3, L929, F9, MC-3T3-E1, PC-12, ROS17/2.8, CHO-K1 and BHK-21. In addition to mammalian cells, a person skilled in the art may suitably select microorganisms such as budding yeast cells, divided yeast cells, and *Escherichia coli* for use by introducing genes by a method in accordance with a given purpose.

In the method of screening according to the present invention, binding between VDR and CDP can be detected as a result of the quantitative or kinetic increase in the binding between VDR and CDP caused by the test compound.

Systems for the quantitative analysis of binding between VDR and CDP include methods such as a pull-down assay (Molecular and Cellular Biology, October 2004, p. 8847-8861) or methods of immuno-precipitation (The Journal of Biological Chemistry, Vol. 276, Issue 31, 28835-28841, Aug. 3, 2001). For example, in the pull-down assay, GST-VDR prepared in accordance with Example 2 and a cellular nuclear extract which is purified or which contains CDP are reacted in the presence or the absence of a vitamin D derivative or other compound. GST-VDR is precipitated using a glutathione binding resin. A detection method for the bound CDP such as western blotting as described in Example 3 is used to determine the amount of CDP bound with VDR.

Systems enabling the kinetic analysis of VDR-CDP binding also include a method using a surface plasmon resonance method (The Journal of Biological Chemistry Vol. 278 Issue 15, 13271-13277, Apr. 11, 2003). This method may be employed in a Biacore (registered trademark) (Biacore AB) Protein Interaction Analysis System by fixing VDR to a sensor chip and after reacting with or placing in the presence of a vitamin D derivative or other test compound, the compound is reacted with purified CDP or a cellular nuclear extract containing CDP to produce a signal, which enables measurement of the binding rate and dissociation rate between VDR and CDP or the level of CDP binding to VDR. A compound displaying a larger binding rate and/or a smaller dissociation rate in the kinetic analysis is evaluated as a compound promoting binding of VDR and CDP.

An example of another screening system for detecting binding of VDR and CDP is a method such as fluorescent resonance energy transfer (FRET) (The Journal of Biological Chemistry, Vol. 275, Issue 52, 41114-41123, Dec. 29, 2000). For example, VDR and CDP are expressed as fusion proteins with green fluorescent protein (GFP) and blue fluorescent protein (BFP). The binding of VDR and CDP can be detected when reacted with the test compound in the presence of the fusion protein. The increase in binding between VDR and CDP can be determined by measuring the decrease in the light intensity of the florescent wavelengths (about 435-485 nm) of BFP and/or the increase in the light intensity of the florescent wavelengths (about 515-555 nm) of GFP based on incident excitation light at an excitation wavelengths (about 370-390 nm) for BFP which is expressed as a fusion protein. Further, the rate of VDR and CDP binding can be determined in the presence of both the VDR fusion protein and the CDP fusion protein after reaction with the test compound by measuring the decrease in the light intensity at fluorescent wavelengths of BFP and/or the increase in the light intensity at florescent frequencies of GFP. When intracellular VDR fluorescent protein and CDP fusion protein are expressed and reacted with the test compound, observation of binding between VDR and CDP at localized intracellular positions, for example in the nucleus is possible using a fluorescence microscope, and when an image analyzer is added, measurement of the fluctuation in the fluorescence intensity is possible.

Although a cell producing both VDR and CDP or a cellular preparation of such cells can be used in systems for performing quantitative analysis of binding between VDR and CDP, it is possible to use a purified sample of either VDR or CDP. Methods of producing preparations of purified VDR or CDP include production of a vector combining genes encoding for the VDR and CDP proteins in a suitable expression vector adapted to express the proteins, after preparation of transformants by introduction into microorganisms such as animal cells, plant cells, insect cells, yeast or *E coli* and culturing the transformants. Methods of production include methods of acellular protein synthesis such as in vitro translation reaction systems. For example, sequences controlling transcriptional regulation, preferably SP6 promoters, T3 promoters or T7 promoters are added upstream of the 5' end of the genes encoding for VDR or CDP proteins. RNA molecules coding for VDR or CDP proteins are prepared by intracellular or in vitro transcription of those genes and then a cellular extract is used for in vitro transcription reactions which is prepared from wheat germ, *E. coli* or blood reticulocytes (Sawazaki et al., Tanpakushitsu, Kakusan, Koso; 2003, 48, p. 549-554). VDR or CDP produced by these types of transformants or acellular protein synthesis can be purified or separated using various separation operations by making use of their physical properties or chemical properties as desired (for example refer to Nihon Seikagakukaihen "Seikagaku Databook II" First Edition, First Issue, Tokyo Kagaku Dojin Jun. 23, 1980, p. 1175-1259; Arakawa et al. (Biochemistry) (USA) Dec. 16, 1986, 25, No. 25, p. 8274-8277 (1986); Langley et al., European Journal of Biochemistry, Germany, Mar. 2, 1987, 163, No. 2, p. 313-321). Such methods include in particular, usual methods of reconstituted processing, processing by protein precipitants, (salting-out methods), centrifugal separation, osmotic shock, ultrasonic fragmentation, ultrafiltration, gel filtration, various types of liquid chromatography such as adsorption chromatography, ion-exchange chromatography, affinity chromatography, high-performance liquid chromatography (HPLC), and dialysis, and combinations of the above methods. Antibodies binding to polypeptides as described above may be used in methods of purification based on polypeptide affinity and are performed by binding and dissociation between the polypeptide and the antibody.

Other examples of method for preparing purified VDR or CDP include producing VDR or CDP by transformants or acellular protein synthesis fused with an affinity tag and then separating and purifying the VDR or CDP. When VDR or CDP is expressed in the form of a fusion protein with an affinity tag, the tag can be used to perform affinity purification. Affinity tags include glutathione-S-transferase (GST) or polyhistidine tags (His tags, Sisk et al., Journal of Virology (USA) February 1994, 68, No. 2, p. 766-775) and FLAG tags (Hopp et al. Biotechnology 1988, 6, p. 1204-1210). When a GST fusion protein fused with GST is used in this method, a glutathione-binding carrier is used and purification performed via the attachment and detachment reactions between GST and the glutathione-binding carrier. When His tag fusion proteins are used, a metal ion chelate carrier is used and purification performed via the attachment and detachment reactions between the His tag and the metal ion chelate carrier. When FLAG tag fusion proteins are used, a carrier binding with an anti-FLAG tag antibody is used and purification is performed via the attachment and detachment reactions between the FLAG tag and the anti-body bound carrier.

In the above screening systems, in addition to comparing the quantitative or kinetic values for VDR and CDP binding resulting from a test compound, comparison is also possible as relative values with values when the test compound is not present or when $1,25 (OH)_2D_3$ or similar compound is used as a reference compound.

Furthermore, candidate compounds selected using the above screening system can be used to verify the effect of the test compound on bone formation by use of a standard such as differentiation of osteoblasts or bone formation capacity in a normal non-human animal or a pathologic animal model. For example, when reacting a candidate compound with cells in an osteoblast system such as HOS cells as described in Example 7, the expression of protein or genes such as osteoblast differentiation markers (alkali phosphatase gene, osteocalcin, or the like) are used as indicators to verify an effect of a candidate compound in increasing bone mass. The effect of a candidate compound such as increasing bone mass in animals, for example, can be verified by administration of the compound to normal non-human animals or pathologic model animals such as animals with ovaries removed and then analyzing the bone tissue in the animal by bone mass density (BMD), MicroCT or tissue sample. In this manner, activity of a candidate compound such as bone mass increasing activity can be verified. (Jpn. J. Pharmacol. VOL. 89, p. 255-266 2002).

The present invention relates to a screening method for compounds that increase the transcriptional activity by a complex of VDR and CDP including a step of detecting an increase in transcriptional activity by a complex of VDR and CDP in the presence of a test compound. The present invention is based on the insight that VDR-mediated transcriptional activity and CDP-mediated transcriptional activity increase in a VDR ligand-dependent manner. Since VDR-mediated transcriptional activity and CDP-mediated transcriptional activity are increased in the presence of VDR ligands, VDR ligands are cited as one example of a compound selected by the screening system of the present invention. The object of the screening method of the present invention is the identification of compounds that increase the transcriptional activity by a complex of VDR and CDP. Consequently, in addition to VDR ligands, compounds screened using the screening method of the present invention include compounds displaying affinity to CDP.

The term "transcriptional activity by a complex of VDR and CDP" as used in the present specification refers to transcriptional activity induced specifically by the formation of a complex by binding between VDR and CDP and, more precisely, transcriptional activity displayed in osteoblasts. The formation of a complex between VDR and CDP was not seen in cells other than osteoblasts such as HeLa cells which are uterine cancer cells or MCF-7 cells which are mammary cancer cells, but was observed in osteoblasts. Consequently, transcriptional activity in such complexes promotes osteoblast differentiation and is expected to have a weak effect in increasing calcium blood levels.

The step of detecting an increase in the transcriptional activity by a complex of VDR and CDP can be performed by over-expression of CDP, by detecting a further increase in the VDR-mediated transcriptional activity, by over-expression of VDR, or by detecting a further increase in CDP-mediated transcriptional activity.

Although the term "VDR-mediated transcriptional activity" as used in the present specification refers to transcription of VDR recognizing sequences induced by VDR activity, there is no particular limitation on such activity as long as the transcriptional activity is produced specifically by the formation of a complex resulting from binding between VDR and CDP. The evaluation of any increase resulting from VDR-mediated transcriptional activity can be performed by evaluating the transcription of DNA regions containing VDR recognition sequences. VDR-mediated transcriptional activity can be measured using a reporter gene assay system by artificially leaving VDR (DEF region) (hereafter sometimes abbreviated to VDR (DEF)) required for receptor activity other than DNA binding activity and substituting VDR DNA-binding regions with transcription regulation genes used in the laboratory such as GAL4 DNA binding domain. This type of reporter gene assay system is preferred from the point of view of decreasing reactions resulting in noise produced respectively by VDR, CDP and the test compound. A person suitably skilled in the art may construct a screening system using transcriptional activity as an indicator by selecting other methods including a two-hybrid assay method using mammalian cells (The Journal of Biological Chemistry, Vol. 274, Issue 45, 32376-32381, Nov. 5, 1999) or a two-hybrid assay method using yeast cells (Molecular Endocrinology Vol. 11, No. 3, p. 366-378, 1997).

Although the term "CDP-mediated transcriptional activity" as used in the present specification refers to transcription of CDP recognizing sequences induced by CDP activity, there is no particular limitation on such activity as long as the transcriptional activity is produced specifically by formation of a complex resulting from binding between VDR and CDP. The evaluation of any increase resulting from CDP-mediated transcriptional activity can be evaluated by evaluating the transcription of DNA regions including CDP recognition sequences. CDP-mediated transcriptional activity can be measured using a reporter gene assay system in the same manner as VDR-mediated transcriptional activity described above.

VDR ligands that increase VDR-mediated transcriptional activity by over-expression of CDP also increase expression of the osteocalcin gene and the alkali phosphatase gene which are osteoblast differentiation markers. Consequently, the screening method according to the present invention enables identification of VDR ligands participating in osteoblast differentiation. Furthermore, since such VDR ligands participate in binding between VDR and CDP present in abundant amounts in osteoblasts, the screening method of the present invention enables the identification of VDR ligands having potent bone formation effects acting selectively on osteoblasts with few side effects such as hypercalcemia.

The screening method of the present invention can be performed using cells producing and/or expressing both VDR and CDP. Osteoblast-like cells as described above are an example of cells producing and/or expressing both VDR and CDP. Since a cell used in screening according to the present invention may be any cell producing and/or expressing both VDR and CDP, cells having at least one of VDR genes and CDP genes introduced therein may also be used.

As described above, the method of screening according to the present invention can use a reporter gene assay system to measure the increase in transcriptional activity by a complex of VDR and CDP. A reporter gene is a guiding gene inserted into DNA to check the transcriptional activity of a promoter or an enhancer. There is no particular limitation on the reporter gene as long as it enables measurement of a relevant level of expression and any gene capable of simple detection and quantification is generally preferred. Reporter genes include luciferase genes, CAT (chloramphenicol acetyltransferase) genes, β-Gal (β-galactosidase) genes, hGH (secreted human growth hormone) genes, SEAP (human secreted alkaliphosphatase) genes, GFP (green fluorescent protein) genes and GUS (β-glucuronidase) genes.

An assay using a reporter gene may be suitably selected by a person skilled in the art. For example, an assay using a luciferase gene as a reporter gene can be used to evaluate an increase in CDP-mediated transcriptional activity or VDR-mediated transcriptional activity by causing a luminescence reaction by application of oxygen and a substrate to a cell extract solution, determining the level of luminescence and evaluating the level of expression of luciferase.

The increase in transcriptional activity of the complex of VDR and CDP can be measured using expression of an osteoblast differentiation marker gene or a VDR target gene as an indicator. A CYP24 gene may be cited as the VDR target gene. When an increase in expression of the VDR target gene is detected, it is determined that VDR has been activated and VDR-mediated transcriptional activity has increased. The osteoblast differentiation marker gene includes an osteocalcin gene and an alkaline phosphatase gene. When an increase in expression of the osteoblast differentiation marker gene is detected, it is determined that osteoblast differentiation has been induced due to the result that VDR has been activated and VDR-mediated transcriptional activity has increased, or due to the result that CDP has been activated and CDP-mediated transcriptional activity has been increased, or due to the result that VDR or CDP-mediated transcriptional activity has increased by a complex of VDR and CDP.

Furthermore, the effect of candidate compounds selected using the above screening system on bone formation can be verified by use of a standard such as differentiation of osteoblasts or bone formation capacity in a normal non-human animal or a pathologic animal model. For example, when reacting a candidate compound with cells in an osteoblast system such as HOS cells as described in Example 7, the expression of proteins or genes such as osteoblast differentiation markers (osteocalcin, alkaline phosphatase or the like) are used as indicators to verify an effect of a candidate compound for increasing bone mass. The effect of a candidate compound in animals for example can be verified by administration of the compound to normal non-human animals or pathologic model animals such as animals with ovaries removed and then analyzing the bone tissue in the animal by bone mass density (BMD), MicroCT or tissue sample. In this manner, activity of a candidate compound such as bone mass increasing activity can be verified (Jpn. J. Pharmacol. VOL. 89, p. 255-266 2002).

The method of screening as described above is expected to identify compounds participating in osteoblast differentiation and/or compounds selective for osteoblasts with low levels of side effects such as hypercalcemia. The compound preferably displays an effect of increasing bone mass in animals.

Compounds selected using the above method of screening according to this invention relate to compounds having affinity for VDR and/or CDP, compounds increasing the binding between CDP and VDR quantitatively or kinetically, or compounds increasing the transcriptional activity by complexes of VDR and CDP. For example, such compounds include VDR ligands, compounds having affinity for VDR, CDP ligands, or compounds having affinity for CDP. More precisely, such compounds include for example vitamin D derivatives. However, there is no particular limitation on the compounds as long as the compound increases quantitatively or kinetically the binding between VDR and CDP or a compound which increases the transcriptional activity by a complex of VDR and CDP.

The present invention relates further to therapeutic agents including the above compounds for diseases involved in the increases in VDR-mediated transcriptional activity of complexes of VDR and CDP. Diseases involved in the increases in VDR-mediated transcriptional activity due to binding of the CDP include, for example, metabolic bone diseases, diseases characterized by abnormal cellular differentiation and/or cell proliferation, acne, alopecia, Alzheimer's disease, autoimmune diabetes, fracture healing, breast cancer, prostate cancer, cancer of the large intestine, brain cytomas, bone cancer, melanoma, myelofibrosis, primary hyperparathyroidism, type-1 diabetes, host versus graft reaction, graft versus host reaction, transplant tissue rejection, steroid-induced cutaneous atrophy, humoral hypercalcemia, induced diabetes, leukemia, lupus, multiple sclerosis, insufficient production of sebum, osteomalacia, osteoporosis, lack of skin firmness, lack of skin hydration, phoriatic arthritis, psoriasis, renal failure, renal osteodystrophy, scleroderma, autoimmune chronic skin disorders, discoid or systemic lupus erythematosus and articular rheumatism. Furthermore, since method of screening as described above is expected to identify compounds participating in osteoblast differentiation and/or compounds selective for osteoblasts with low levels of side effects such as hypercalcemia, some of such compounds shall be useful as therapeutic agents for diseases in which differentiation of osteoblasts is promoted or diseases having the effect of increasing bone mass. A typical example of such diseases is metabolic bone diseases. Metabolic bone diseases include osteoporosis, Paget's disease, osteomalacia, neoplastic osteomalacia, osteopetrosis and renal osteodystrophy. The compounds identified by the screening method of the present invention are expected to be compounds participating in osteoblast differentiation and/or compounds selective for osteoblasts with low levels of side effects such as hypercalcemia, in particular such compounds should be useful as therapeutic agents for osteoporosis.

The present invention relates further to a kit for performing the screening method comprising at least one of (a) a vector containing a VDR recognition sequence and a reporter gene for evaluating an increase in VDR-mediated transcriptional activity; and (b) a vector containing a CDP recognition sequence and a reporter gene for evaluating an increase in CDP-mediated transcriptional activity; and (c) a reagent for detecting a product of the reporter gene. The kit enables simple screening to be performed. The kit may include a cell transcribing both VDR and CDP.

Another aspect of the kit relates to a kit for performing a screening method, comprising (a) a VDR recognition sequence, a CDP recognition sequence, and a vector containing a reporter gene for evaluating an increase in transcriptional activity by a complex of VDR and CDP; and (b) a reagent for detecting a product of the reporter gene. The gene transcription regulation region in the genomes of higher animals contains recognition sites for a plurality of transcription control factors which combine to control gene transcription. As a result, a vector binding a reporter gene to a regulation region containing both a VDR recognition sequence having a VDR recognition site and a CDP recognition sequence can be used for determining the transcription activity by a VDR and CDP complex.

A VDR recognition sequence refers to a DNA sequence to which VDR binds due to the specific action of a VDR ligand, and preferably to a sequence which binds VDR in a complex of VDR and CDP. Sequences of this type of VDR recognition site include base sequences such as two VDR recognition sequences existing in a promoter/enhancer region of human CYP24: GCAGGTCAGCGAGGGCG (SEQ ID NO: 1) and GGAGTTCACCGGGTGTG (SEQ ID NO: 2(Chen KS et al. Biochem. Biophys. Acta. 1263: 1-9 (1995)) or the VDR recognition sequence in human osteocalcin promoter: CC GGGTGAACGGGGCA (SEQ ID NO: 3) (Ozono K et al. J. Biol. Chem. (1990) 265:21881-21888)/TT TGGTGACTCACCGGGTGA (SEQ ID NO: 4) (Morrison NA et al. Science (1989) 265: 21881-21888) /TT TGGTGACTCACCGGGTGAACGGGGGCA (SEQ ID NO: 5) (Schrader M at al. J. Biol. Chem. (1994) 269: 5501-5504) (The underlined sections in the sequences are section considered important for binding of VDR). However, a VDR recognition sequence refers to a DNA sequence to which VDR binds due to the specific action of a VDR ligand and preferably, the term is not limited to the above examples as long as it is a sequence which binds a complex of VDR and CDP. A person skilled in the art may combine parts of the above sequences, introduce variant bases or select other sequences (Vitamin D, 2nd Edition, Feldman, Pike, Glorieux, (eds.) p311-325).

The above CDP recognition sequences refer to DNA sequences to which CDP binds specifically or preferably to regions to which CDP binds in a complex of VDR and CDP. These types of sequences include all types of the so-called CCAAT box sequences, that is to say, combinations of CCAAT or CCGAT and CAAT or CGAT or sequences containing base sequences such as ATCGAT. However, the CDP recognition sequences are not limited to the above, and a person skilled in the art may combine parts of the above sequences, introduce variant bases or select other sequences (Alain Nepveu. Gene VOL. 270, 2001, p1-15). It is possible to evaluate whether or not CDP-mediated transcription activity has been increased by evaluating the transcription of a DNA region containing the CDP recognition sequence.

"A reagent for detecting a product of the reporter gene" may be selected as required from substrates for detecting reporter products, cell fixation solution, cell lysate, or a buffer solution for diluting a reagent. For example, when the reporter gene used includes luciferase genes, CAT (chloramphenicol acetyltransferase) genes, β-Gal (β-galactosidase) genes, SEAP (human secreted alkaline phosphatase) genes and GUS (β-glucuronidase) genes, the substrate for detecting the reporter product is a substrate reacting with respective enzymes and commercially available substrates can be used for each enzyme. Thus, the level of induction of expression of the reporter gene can be measured by the substrate reaction. The measurement can be performed by measuring a parameter such as radioactivity, color development, fluorescence, luminescence and the like, in response to the type of substrate. When product resulting from reporter gene expression is a protein, it may be measured using methods of immunological determination such as EIA or ELISA methods and suitable reagents may be selected by a person skilled in the art for that purpose. Furthermore, expression of the reporter gene can be determined using transcription products such as mRNA and suitable reagents such as primer probes or competitive probes may be selected by a person skilled in the art for that purpose.

In addition, the kit may include as required additional elements such as positive controls, negative controls, reaction vessels, filters for optical analysis, and instructions describing assay protocols. These elements can be suitably mixed in advance as required. Furthermore, preservatives or antiseptic agents may be added to each element as required.

A kit for performing the above screening may use methods such as a One-hybrid system using mammalian cells, a Two-hybrid system or a yeast-based Two-hybrid system. A person skilled in the art may construct a kit in a form adapted to the selected screening method.

EXAMPLES

The invention will be described in further with reference to the examples. However, the invention is not limited to these examples.

Example 1

Purification of Protein Complex of Fusion Proteins Between VDR and Glutathione-S-Transferase (GST)

Firstly, GST-VDR which is a bait protein was expressed in *E coli*. With respect to rat VDR sequences reported by Kitagawa et al., Cell, Vol. 113, 905-917, 2003, *E coli*. (DH5alpha strain) transformed using either a pGEX4T-1 vector containing the ligand binding region (Amersham Biosciences) or a pGEX4T-1 vector containing DNA sequences encoding the human VDR ligand binding region (DEF region) (The structure of the VDR domain is explained in J Wesley Pike et al. The Vitamin D Receptor. (2005) Vitamin D, 2nd Edition, Feldman, Pike, Glorieux (eds.) p. 167-191) was cultured in 2 L of LB medium at 37° C., while shaking at 120 revolutions. When the absorbance at 600 nm reached 0.4-0.5, 0.1 mM isopropyl-1-thio-β-D-galactopyranoside (IPTG) was added to the culture and culturing was continued for 3 hours at 27° C. while shaking at 120 revolutions in order to induce GST-VDR protein expression. Thereafter, cells were collected by centrifuging. The cells were suspended by adding 100 mL of PBS(-) and sonicated. To the resulting mixture was added 20% triton X-100/PBS(-) at one part for every twenty parts of the solution. The cells were homogenized by gentle inversion mixing at 4° C. for 30 minutes. After centrifuging at 4° C., 1000×g for 5 minutes, GST-VDR can be obtained from the soluble fraction of the supernatant. This solution was inversion mixed at 4° C. overnight with Glutathione Sepharose 4B (Pharmacia Biosciences) washed at least three times in PBS (-). Subsequently, the solution was washed at least five times in approximately 5 mL of PBS(-), and a resin in which GST-VDR protein is bound to Glutathione Sepharose 4B (hereafter "GST-VDR resin") was prepared. For comparison, a GST resin was also prepared using the same operation with a vector expressing only GST not fused with VDR. A 5 microliter-aliquot of SDS sample buffer (TrisSDS, β-ME sample buffer, Daiichi Pharmaceuticals, Product No. 301780) was diluted twice using water and thereafter 5 microliters was added to the resin and the resultant mixture was heated in a water bath at 98° C. for two minutes, SDS-PAGE performed for the bound protein under reducing conditions (SDS polyacrylamide gel phoresis), staining performed using Coomassie brilliant blue (CBB) in order to make the protein visible as shown in FIG. 1. GST-VDR resin was prepared allowing for detection of approximately 26 kDa of GST protein in Lane 2 and approximately 60 kDa of GST protein in Lane 3. A molecular weight marker was run in Lane 1.

Example 2

Identification and Purification of Protein Bound to GST-VDR (DEF)

Figure 2:
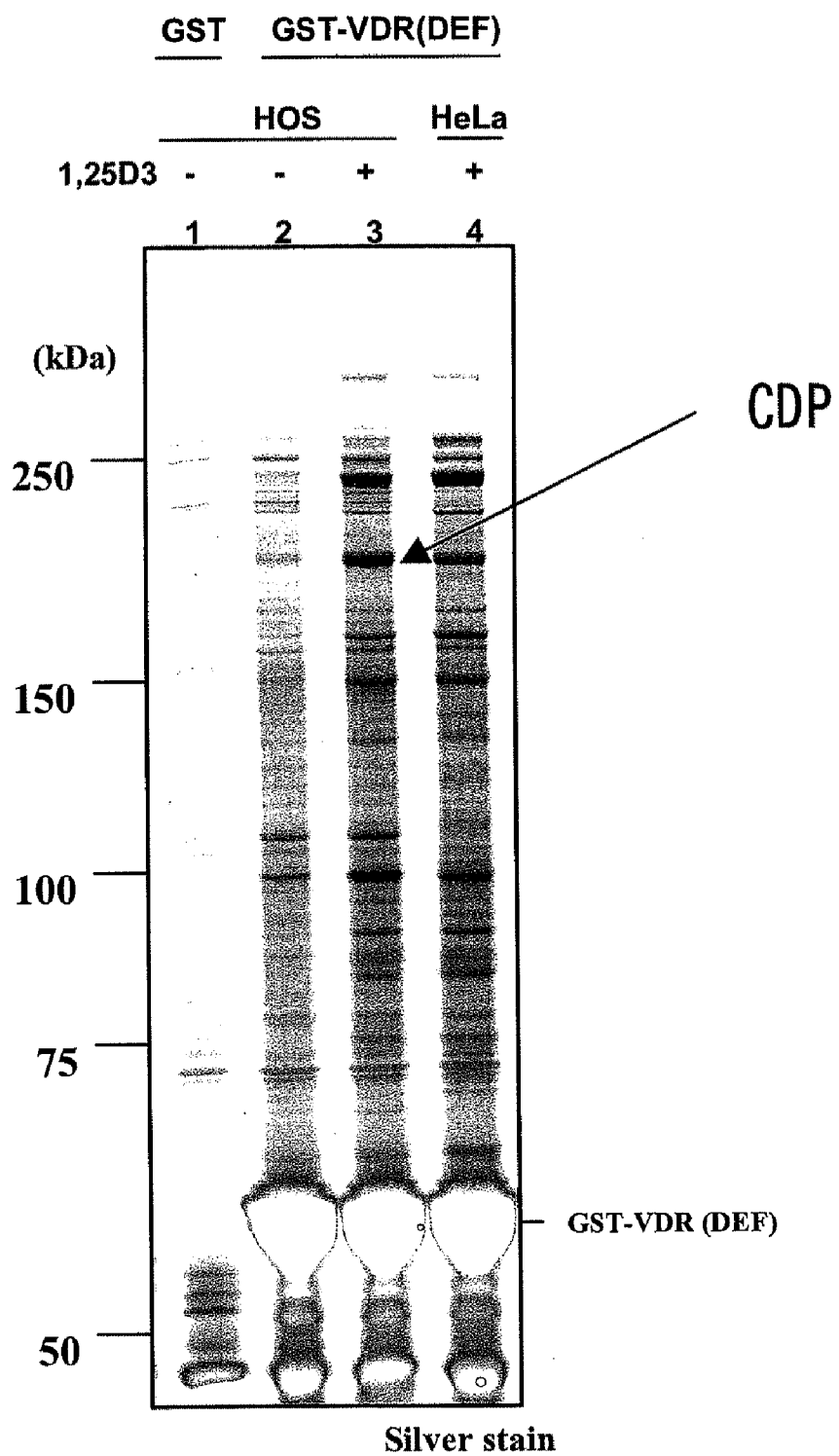
FIG. 2 is an Ag-stained image of an eluted resin-bound protein after mixing a nuclear protein extract from HOS cells and HeLa cells overnight with GST-VDR (DEF) resin in the presence and the absence of 1,25 $(OH)_2D_3$.

In accordance with a method described in Dignam J D. et al., Nucleic Acids Research, 1983, Vol. 11, No. 5 1475-1489, a nuclear protein extract was prepared from HOS cells which is a human osteoblast cell strain (obtained from ATCC, Number CRL-1543). The resulting nuclear protein extract was dissolved in buffer D (20 mM HEPES, 10% glycerol, 0.15 M KCl, 0.2 mM EDTA, 0.5 mM PMSF, 0.01% 2-mercaptoethanol (pH=7.9). The nuclear protein extract was mixed for one hour or overnight with GST-VDR resin either in the presence or absence of $1,25(OH)_2D_3$ which is a VDR ligand. The GST-VDR resin was washed and placed in a state in which only a specifically binding protein was bound to the GST-VDR resin. The protein bound to the resin was eluted using a reduced glutathione solution (pH=8.0) having a concentration of 15 mM on the GST-VDR resin. The eluted protein was subjected to SDS-PAGE under reducing conditions in the same manner as Example 1. Thereafter the gel was stained using silver staining (SilverQuest™, Silver Staining Kit:Invitrogen) to obtain the results in FIG. 2. The protein bands detected only in the presence of a ligand in Lane 3 or those detected more strongly than in Lane 2 are proteins binding specifically to VDR in the presence of a ligand. After these bands were excised, reduced using DTT, alkylated using iodoacetamide and subjected to trypsin digestion in the gel, the peptides were eluted from the gel, the peptide solution mixed with a-cyano-4-hydroxycinnamic acid and spotted to a target attached to Ultraflex™ (Bruker Daltonics). Qualitative analysis was performed according to the manufacturer instructions and CCAAT Displacement Protein (CDP) was identified by analysis using a method of peptide mass finger printing. Up until this point, it was not known that CDP binds to VDR.

Example 3

Detection of CDP by Western Blotting

Figure 3:
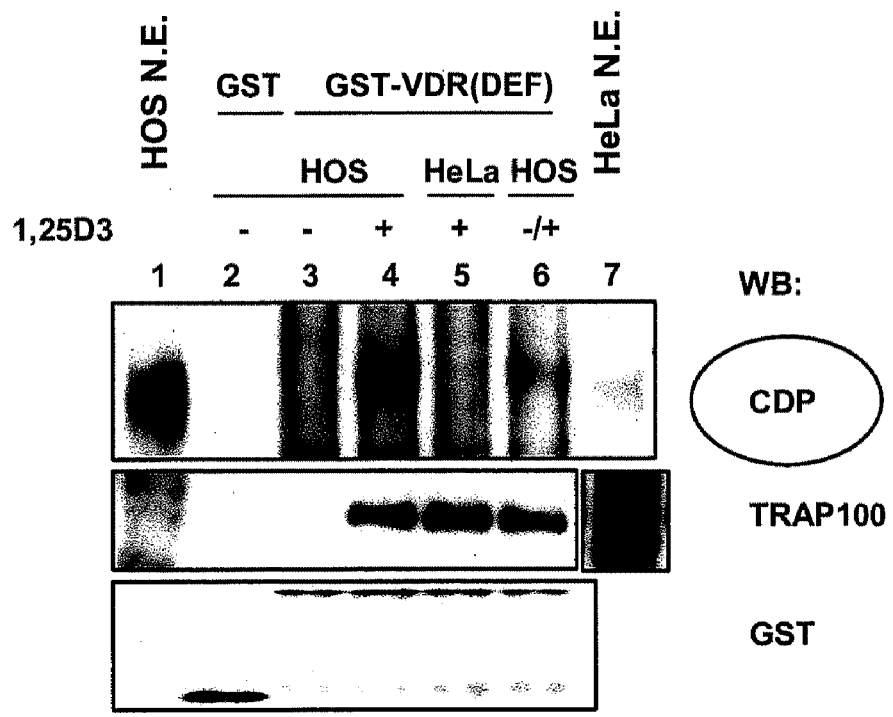
FIG. 3 is a western blot image of an eluted resin-bound protein after mixing a nuclear protein extract from HOS cells and HeLa cells overnight with GST-VDR (DEF) resin in the presence and the absence of 1,25 $(OH)_2D_3$. The images show, from the top row down, detection obtained by using anti-CDP antibody, anti-TRAP100 antibody, and anti-GST antibody.

A part of the eluted liquid from Example 2 was subjected to SDS-PAGE under reducing conditions, blotted to a PVDF membrane (Millipore, Product No. IPVH304F0) and the detection of CDP was performed using standard techniques. The primary antibodies were anti-CDP (M-222) rabbit polyclonal IgG (Santa Cruz Biotechnology, Product No. sc-13024). The secondary antibody was anti-rabbit IgG labeled with HRP (Amersham Biosciences, Product No. NA934V). ECL Plus (GE Healthcare Bioscience, Product No. RPN2132) was used in the detection operation. The results are shown in FIG. 3. Although a CDP band was not detected nearly at all in Lane 3 in the absence of a ligand, a CDP band was strongly detected in Lane 4 in the presence of a ligand. For comparison, a nuclear protein extract from HeLa cells which are uterine cancer-derived cells rather than osteoblasts was obtained in the same manner and mixed with GST-VDR in the presence of a ligand. The elution of the protein bound to reduced glutathione was run in Lane 5. In Lane 5, a CDP band is not visible which demonstrates that binding of CDP to GST-VDR in the presence of a ligand is specific to osteoblasts. On the other hand, although direct GST-VDR binding is not observed, TRAP100 is known as a factor binding and forming a complex (DRIP complex) with GST-VDR in the presence of a ligand (Rachez et al., Genes and Development, 1998, 12, 1787-1800). TRAP100 was detected using western blotting in the same manner using anti-TRAP100 goat IgG (C-16) (SantaCruz Biotechnology, Product No. sc-5338) as a primary antibody and anti-goat IgG HRP (DAKO, Product No. P0449) as a secondary antibody. TRAP100 was confirmed both in HOS cells (Lane 4) and when the nuclear protein extract prepared from HeLa cells was used (Lane 5) as long as a ligand was present. These results show that proteins such as TRAP100 bind and form ligand-dependent complexes with GST-VDR irrespective of the cell type. Nuclear protein extracts of HOS cells and HeLa cells were run in Lane 1 and Lane 7. This comparison shows that the amount of the CDP protein present in nuclear protein extracts is higher in HOS cells than HeLa cells.

Example 4

Direct Binding of CDP and VDR by GST-Pulldown Assay

Figure 4:
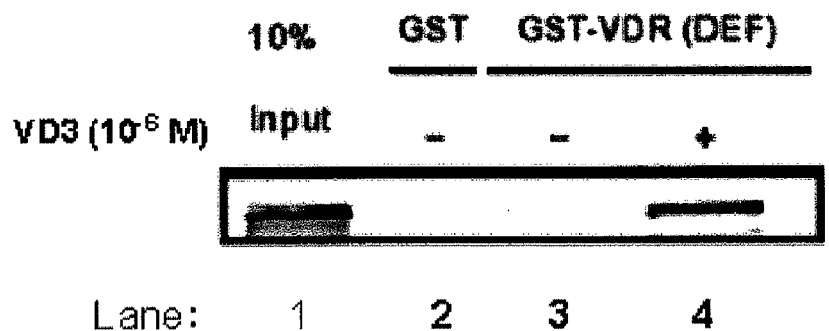
FIG. 4 is an SDS-PAGE image detected using $^{35}S$ after placing $^{35}S$-labelled CDP in the presence of GST-VDR (DEF) resin in the presence and the absence of 1,25 $(OH)_2D_3$.

A CDP protein labeled with $^{35}S$ was synthesized in a 1.5 mL tube using a TnT SP6 Coupled Reticulocyte Lysate System (Promega, Product No. L4600). Template DNA was obtained from Openbiosystem (Product No. EHS1001-7516597) with a sequence (GenBank Acc. BC066592) encoding CDP inserted into a multicloning site downstream of a SP6 promoter of a pSPORT6 vector (Invitrogen) (pSPORT6-CDP). A 25 μL-aliquot of glutathione sepharose 4B resin bound to GST or GST-VDR and the CDP protein labeled with $^{35}S$ were mixed for one hour at 4° C., in NET-N+buffer (50 mM Tris-HCl (pH 7.5), 150 mM NaCl, 5 mM EDTA, 0.5% NP40) either in the presence or absence of $10^{-6}$ M $1,25(OH)_2D_3$. The resulting resin was centrifuged, the supernatant removed and the resin washed three times in NET-N+buffer. SDS sample buffer was added to the resin and SDS-PAGE performed using 10% modified acrylamide gel under reducing conditions. The gel was dried, and CDP labeled with $^{35}S$ was detected using a bioimaging analyzer (Fuji Film, Product No. BAS1500). The results are shown in FIG. 4. Binding of CDP labeled with $^{35}$S was not observed in a resin bound only to the GST protein (Lane 2) or in a GST-VDR (DEF) resin in the absence of a ligand (Lane 3). However, binding of CDP labeled with $^{35}$S was observed only under the conditions of a ligand being present (Lane 4). These results show that CDP binds to VDR in a ligand-dependent manner.

Example 5

Gene Expression of CDP During Osteoblast Differentiation

SaM-1 cells which are cells originating in the human periosteum (Koshihara Y et al. (1987) Biochem Biophys Res Commun 145:651-7, Koshihara Y et al. (1989) In Vitro Cell Dev Biol 25:37-43, Togari A et al. (1997) Neurosci Lett 233:125-8) were cultured for 28 days in Minimum Essential Medium Alpha Medium (Invitrogen, Product No. 12571-071), 10% fetal bovine serum, kanamycin 0.1 mg/mL, and 2 mM α-glycerophosphate (Tokyo Chemical Industry, Product No. G0096) in the presence or absence of 1,25 (OH)$_2$ D$_3$ at various concentrations. The medium was replaced every 2 to 3 days. Cells were recovered at the fourth day, seventh day, fourteenth day, and twenty-eighth day until the final differentiation (calcification) on the twenty-eighth day. Total RNA was extracted using an RNeasy Mini Kit (QIAGEN, Product No. 74104) and cDNA synthesized using an Ommniscript RTKit (QIAGEN, Product No. 205110). The cDNA was mixed with SYBR Green PCR Master Mix (Applied Biosystems, Product No. 4367659) and primer oligos suitable for amplifying various types of genes. Variation in the gene expression of the alkaline phosphatase which is a marker for osteoblast differentiation, CDP and osteocalcin, and beta actin which is known as a universally expressed housekeeping gene was examined by real-time RT-PCR using a GeneAmp 5700 Sequence Detection System (Applied Biosystems) or ABI PRISM 7000 Sequence Detection System (Applied Biosystems). Oligos complementary to the various genes were designed by general methods and synthesized by Sigma Genosys. The results are shown by relative values with respect to the amount of expression of beta actin. The CT value for osteocalcin and CDP (the cycle number when a detectable amplification threshold was reached) was standardized with respect to the amount of expression of human beta actin (Applied Biosystems) by ΔΔCT. The value for the relative amount of expression is calculated using the formula $2^{-(\Delta\Delta CT \text{ of target gene} - \Delta\Delta CT \text{ of beta actin})}$.

Figure 5A:
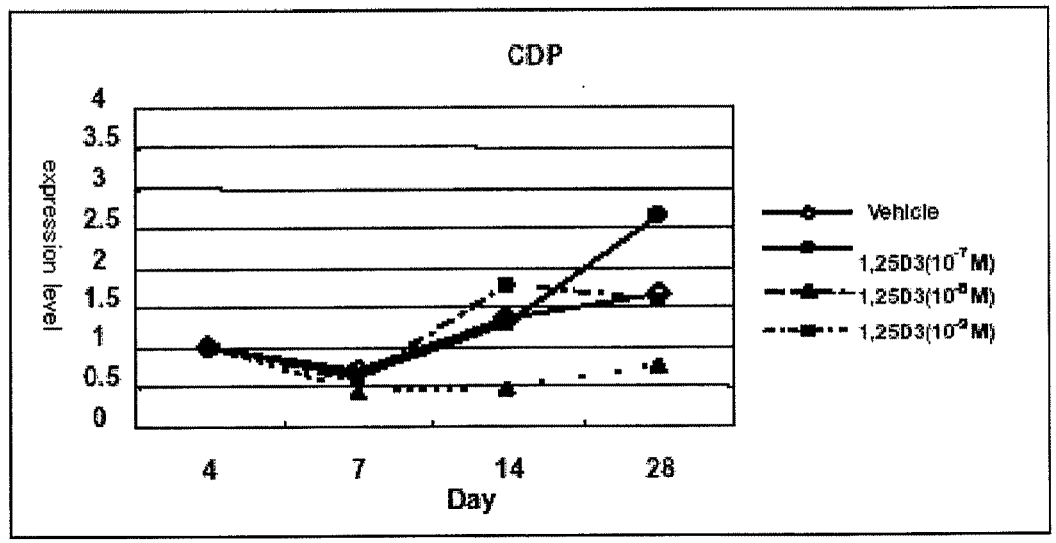
FIG. 5A shows variation in the level of expression of the CDP gene in cells cultured using real-time RT-PCR when SaM-I cells are cultured in the presence of 1,25 $(OH)_2D_3$ at various concentrations.
Figure 5B:
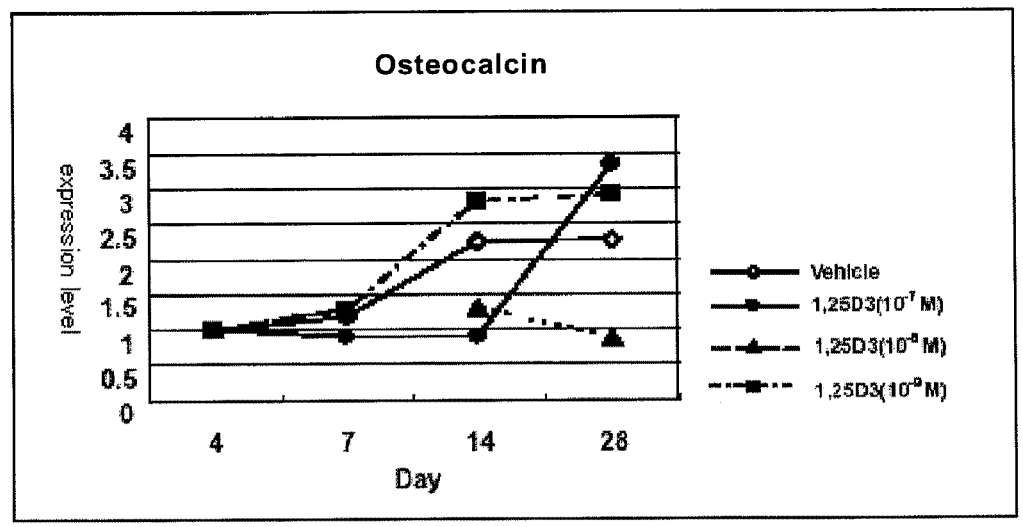
FIG. 5B shows variation in the level of expression of the osteocalcin gene in cells cultured using real-time RT-PCR when SaM-I cells are cultured in the presence of 1,25 $(OH)_2D_3$ at various concentrations.

As shown in FIG. 5, an increase in the gene expression of osteocalcin which is a marker for osteoblast differentiation (FIG. 5B) and gene expression of CDP (FIG. 5A) are observed. These results suggest that CDP participates in osteoblast differentiation by stimulating 1,25 (OH)$_2$D$_3$.

Example 6

Effect of CDP on VDR-Mediated Osteoblast-Selective Transcription Activity

Figure 6A:
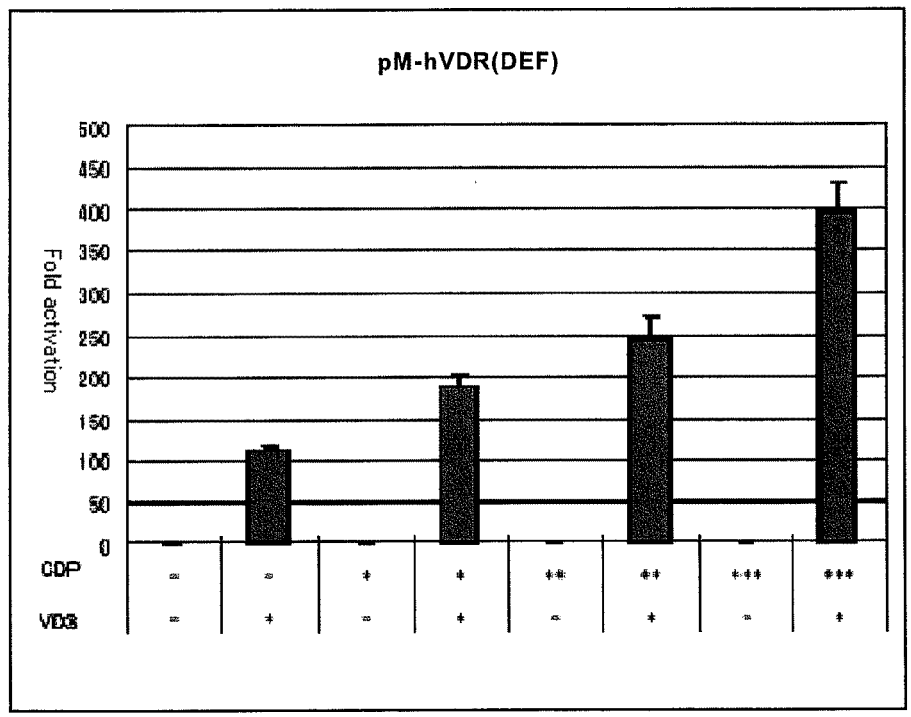
FIG. 6A shows the results of evaluating VDR (DEF)-mediated transcriptional activity potential using a pM-VDR (DEF) plasmid in the presence or the absence of 1,25 $(OH)_2D_3$ or the presence or the absence of CDP.
Figure 6B:
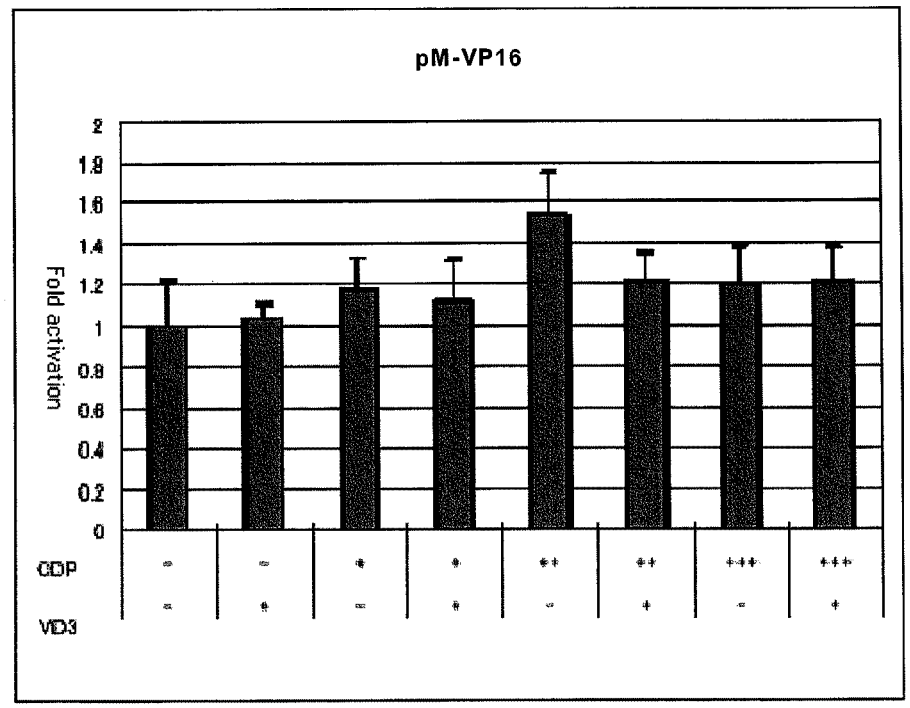
FIG. 6B shows the results of evaluating VP16-mediated transcriptional activity potential using a pM-VP16 plasmid in the presence or the absence of 1,25 $(OH)_2D_3$ or the presence or the absence of CDP.

In order to determine whether or not CDP expression increases VDR ligand-dependent transcription activity, a dual luciferase assay was performed using transient transfection. The reporter vector used in the dual luciferase assay was a pGL3 vector containing a sequence of 5 repeated 17-mer UAS sequences upstream of the luciferase gene. The pGL3 vector was commercially obtained from Promega. Furthermore, a DNA sequence encoding a human VDR ligand binding region (DEF region) or a DNA sequence encoding a transcription activation domain for VP-16 which is a herpes virus transcription activation factor were introduced into a pM vector having a GAL4 DNA binding domain (GAL4 DBD) (CLONETECH Laboratories, Inc) in order to construct plasmids pM-VDR (DEF) and pM-VP16. The expression vector for intracellular expression of the CDP protein was the pSPORT6-CDP vector used in Example 4. HOS cells used in the assay were cultured in DMEM medium containing 10% FBS (Invitrogen, Product No. 1185-092) and were passaged every two or three days. The culturing conditions were 37° C., 5% CO$_2$. DMEM medium containing 10% DCC-FBS (charcoal processed FBS) (Invitrogen, Product No. 11054-020) but not containing phenol red and was used in culturing of the HOS cells during the assay. A cell suspension was prepared so that the concentration of HOS cells in a 48-well plate was $8 \times 10^4$ cells/0.25 mL/well. A mixture was prepared using Lipofectamin 2000 (Invitrogen, Product No. 11668-019) as a reagent in order to perform transfection of reporter vectors, various types of pM vectors and expression vectors. The mixture was mixed with the cell suspension and cells in a 0.25 mL-aliquot were placed into each well. After two hours, this was replaced by Vehicle (ethanol) or DMEM medium containing 10% DCC-FBS (charcoal processed FBS) containing 1,25 (OH)$_2$D$_3$ ($10^{-8}$ M) but not containing phenol red. The medium was removed after 24 hours and after washing once in PBS(-), luciferase activity was determined by a Dual-Luciferase Reporter Assay System (Promega, Product No. E1980) using a luminometer (Berthold Japan, Product Name: MicroLumat LB 96V). The results were expressed as a Fold Activation being value represented by (firefly luciferase activity)/(renilla luciferase activity). In FIG. 6A, transcription activation resulting from pM-VDR increases in the presence of 1,25 (OH)$_2$D$_3$ ($10^{-8}$ M) and that activity is further increased when CDP is expressed. In contrast, in FIG. 6B, transcription activation resulting from pM-VP16 shows no relationship to the presence of 1,25 (OH)$_2$D$_3$ ($10^{-8}$ M) and is not affected by the expression of CDP. These results show that CDP transcription activation is selective with respect to VDR.

Example 7

Effect of CDP on Osteoblast Differentiation in HOS Cells

In order to examine the induction of osteoblast differentiation by 1,25 (OH)$_2$D$_3$ when CDP is expressed by HOS cells, pSPORT6-CDP was transfected to HOS cells by using Lipofectamin2000 (Invitrogen) as a reagent. When the cells reached confluence and after the incubation of 24 hours, culturing was performed in Minimum Essential Medium Alpha Medium, 10% fetal bovine serum, 50 µg/mL ascorbic acid, 1,25 (OH)$_2$D$_3$ at various concentrations or in the presence of the vehicle (ethanol). After three days, cells were recovered, and total RNA was extracted using an RNeasy Mini Kit (QIAGEN, Product No. 74104). Reverse transcription reactions were performed by oligo dT primers using SuperScriptlll RT (Invitrogen, 18080-044) and the amount of expression of various genes was determined using real-time RT-PCR (Applied Biosystems, GeneAmp7000). The amount of gene expression was corrected using GAPDH which is a housekeeping gene and shown as a relative figure of GAPDH and the amount of respective gene expression. The formula used is the same as that used in Example 5.

Figure 7B:
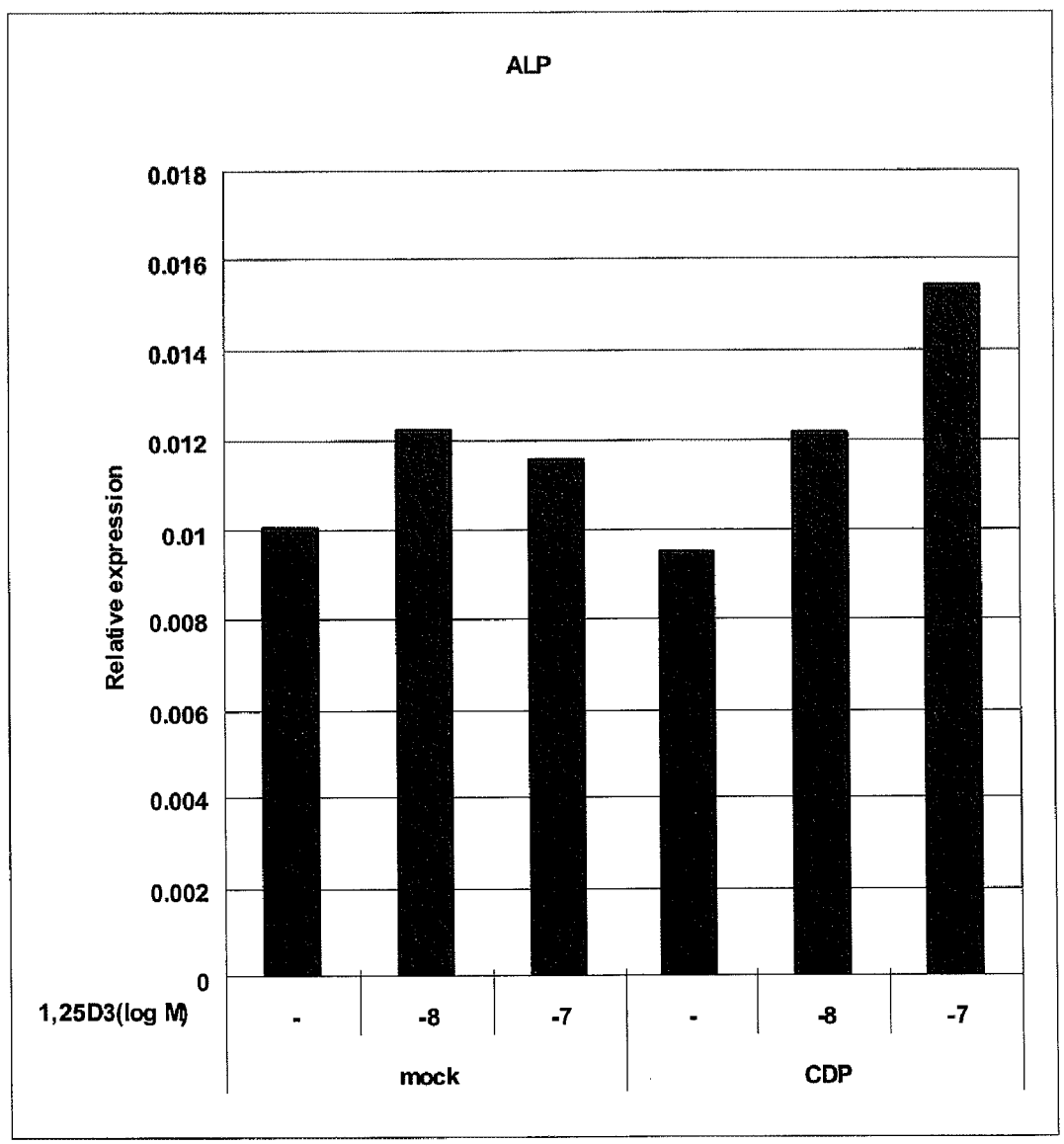
FIG. 7B shows the level of expression of the alkali-phosphatase gene (ALP) in cultured cells when HOS cells containing pSPORT6-CDP are cultured in the presence of 1,25 $(OH)_2D_3$ at various concentrations.
Figure 7C:
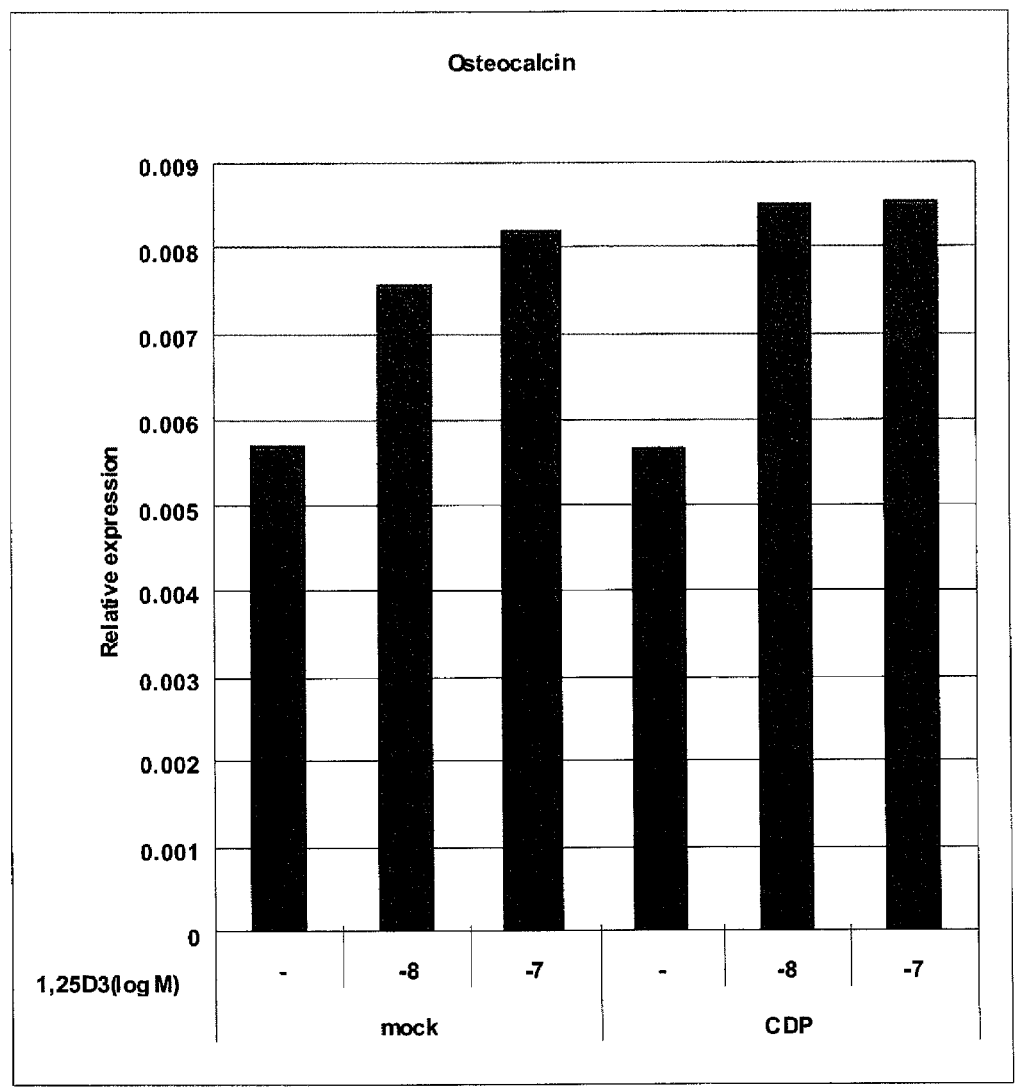
FIG. 7C shows the level of expression of the osteocalcin gene in cultured cells when HOS cells containing pSPORT6-CDP are cultured in the presence of 1,25 $(OH)_2D_3$ at various concentrations.

In the group into which CDP was introduced, gene expression of alkaline phosphatase (ALP) (FIG. 7B) known as a marker for osteoblast differentiation and osteocalcin (FIG. 7C) was increased in addition to CYP24 (FIG. 7A) resulting from 1,25 $(OH)_2D_3$ stimulation. This results suggest that CDP increases osteoblast differentiation by 1,25 $(OH)_2D_3$ stimulation.

Example 8

Effect of CDP on VDR-Mediated VDR Target Gene Expression

Figure 8A:
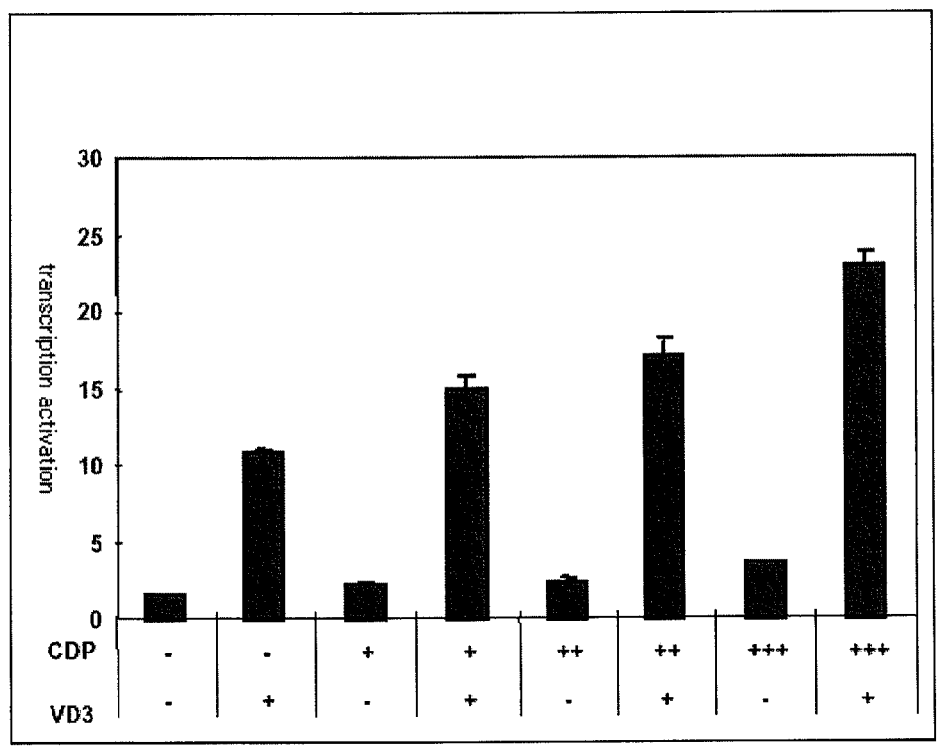
FIG. 8A shows the results of evaluating CYP24 gene promoter transcriptional activity in the presence or the absence of 1,25 $(OH)_2D_3$ or the presence or the absence of CDP.
Figure 8B:
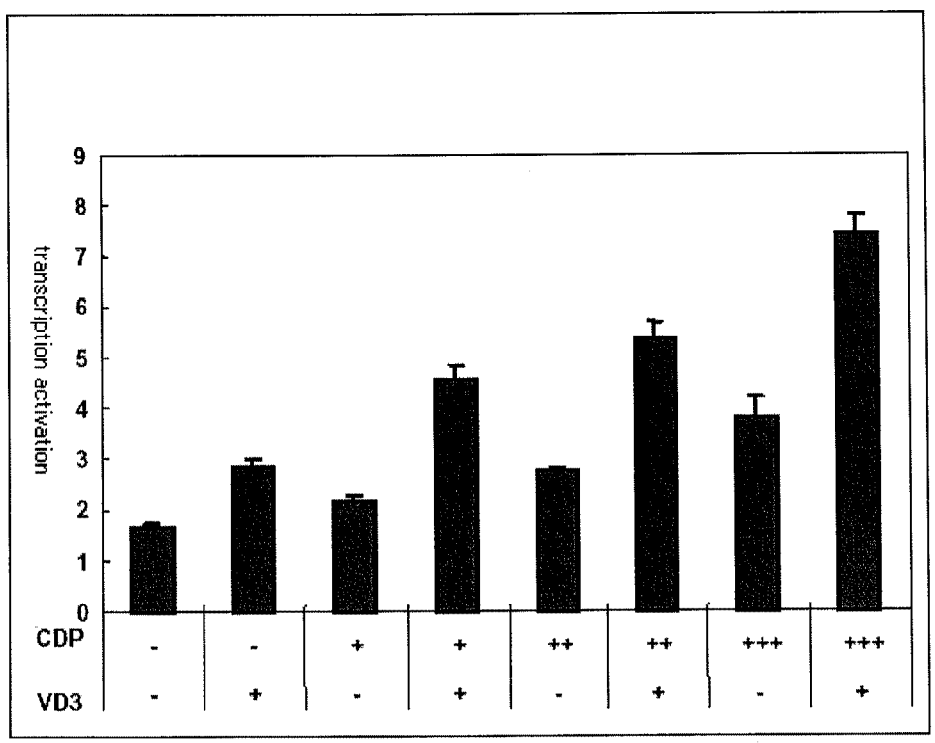
FIG. 8B shows the results of evaluating osteocalcin gene promoter transcriptional activity in the presence or the absence of 1,25 $(OH)_2D_3$ or the presence or the absence of CDP.

In order to determine whether or not CDP expression increases VDR ligand-dependent transcription activity, a dual luciferase assay was performed using transient transfection in the same manner as Example 6. The reporter vector used in the dual luciferase assay was a pGL4 vector containing a sequence of human CYP24 gene promoter or a sequence of a human osteocalcin gene promoter upstream of the luciferase gene. The pGL4 vector was commercially obtained from Promega. Furthermore, a DNA sequence encoding a region of 4-427 amino acid residues for human VDR was introduced into a pTracerCMV2 vector (Invitrogen) in order to construct a human VDR expression plasmid. The expression vector for intracellular expression of the CDP protein was the pSPORT6-CDP vector used in Example 4. HOS cells used in the assay were cultured in DMEM medium containing 10% FBS and were passaged every two or three days. The culturing conditions were 37° C., 5% $CO_2$. DMEM medium containing 10% DCC-FBS (charcoal processed FBS) but not containing phenol red was used in culturing of the HOS cells during the assay. A cell suspension was prepared so that the concentration of HOS cells in a 48 well plate was $8\times10^4$ cells/0.25 mL/well. A mixture was prepared using Lipofectamin 2000 (Invitrogen) as a reagent in order to perform transfection of reporter vectors, various types of expression vectors. The mixture was mixed with the cell suspension and cells in 0.25 mL lots were placed into each well. After two hours, this was replaced by Vehicle (ethanol) or DMEM medium containing 10% DCC-FBS (charcoal processed FBS) containing 1,25 $(OH)_2D_3$ ($10^{-8}$ M) but not containing phenol red. The medium was removed after 24 hours and after washing once in PBS(−), luciferase activity was determined by a Dual-Luciferase Assay kit (Promega) using a luminometer (Bethold Japan). The results were expressed as a "transcription activation" being the value represented by (firefly luciferase activity)/(renilla luciferase activity). In FIG. 8A, VDR-mediated transcription activation of a human CYP24 promoter increases in the presence of 1,25 $(OH)_2D_3$ ($10^{-8}$ M) and that activity is further increased when CDP is expressed. In the same manner, in FIG. 8B, VDR-mediated transcription activation of a human osteocalcin promoter increases in the presence of 1,25 $(OH)_2D_3$ ($10^{-8}$M) and that activity is further increased when CDP is expressed. These results show that VDR-mediated transcription activation is also increased in CYP24 or an osteocalcin promoter which is a naturally occurring VDR target gene. However, in FIG. 8B, the assay is performed using VDR present in the HOS cell without transfecting a VDR expression vector.

Example 9

Ligand-Dependent Binding of VDR and CDP in HOS Cells

Figure 9:
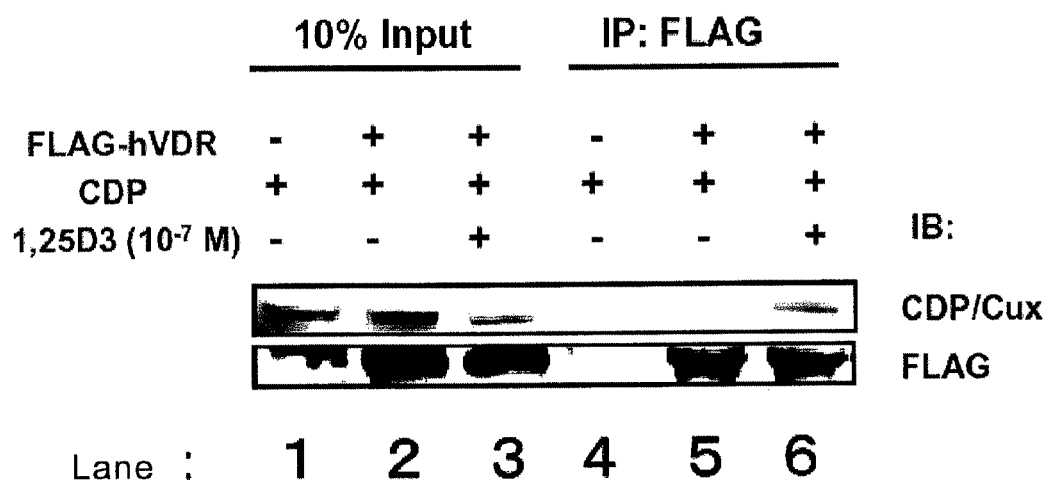
FIG. 9 is a western blot image showing presence or absence of binding between CDP and FLAG-VDR when HOS cells containing both CDP and FLAG-VDR or only CDP are cultured in the presence and the absence of 1,25 $(OH)_2D_3$. The images show, from the top row down, detection obtained by using anti-CDP antibody and anti-FLAG antibody.

In order to examine whether or not CDP actually binds to VDR in the cell in the presence of 1,25 $(OH)_2D_3$, firstly, A FLAG-human VDR(FLAG-hVDR) expression plasmid was constructed by introducing a DNA sequence formed by connecting a DNA sequence encoding a FLAG tag sequence to the N terminal of a DNA sequence encoding human VDR into a pcDNA3 vector (Invitrogen). A plasmid containing one or both of pSPORT6-CDP and FLAG-hVDR was transfected into HOS cells using Lipofectamin2000 (Invitrogen) as a reagent (the samples in FIG. 9 into which the expression plasmid has been genetically introduced are marked as "+" and those samples without any genetic introduced material are marked "−"). After 24 hours, culturing was performed for 24 hours in the presence of DMEM medium containing 10% FBS and including 1,25 $(OH)_2D_3$ at various concentrations or Vehicle (ethanol). Thereafter, the cells were washed in PBS, removed using a scraper and collected by centrifugation. The cells were dissolved in TNE buffer (20 mM HEPES (pH=7.9), 150 mM NaCl, 1% NP40, 1 mM EDTA), centrifuged for 30 minutes at 15000×g at 4° C. and the supernatant used as a cell lysate. Anti-FLAG (registered Trademark) M2 resin (SIGMA, Product No. A2220) was added to the lysate and mixed at 4° C. for three hours in the presence and in the absence of 1,25 $(OH)_2D_3$. Thereafter, the resin was washed in TNE buffer three times, SDS sample buffer added to the resin and SDS-PAGE performed. The method of performing SDS-PAGE and western blotting is the same as that in Example 3. The resulting sample was subjected to SDS-PAGE and CDP and FLAG-VDR were detected using western blotting. The primary antibody against the FLAG peptide was anti-FLAG rabbit IgG (SIGMA) (Product No. F7425). Anti-CDP goat IgG (C-20) (Santa Cruz Biotechnology, Product No. sc-6327) was used to detect the CDP protein. The results are shown in FIG. 9. The "Input" for Lanes 1-3 shows the result for the cell lysate prior to mixing with anti-FLAG antibody resin which was used in SDS-PAGE. The "IP-FLAG" used in Lanes 4-6 shows the results of SDS-PAGE and western blotting on the protein obtained by immuno-precipitation of FLAG-VDR together with the protein binding to FLAG-VDR by mixing with the anti-FLAG antibody resin. Although Lane 6 shows a band of the CDP protein, almost none was detected in Lane 5. On the other hand, FLAG-VDR was detected in a similar manner in both Lanes 5 and 6. In other words, in Lane 6 in which 1,25 $(OH)_2D_3$ is present, FLAG-VDR binds to CDP and is immunoprecipitated as a complex. In Lane 5 in which 1,25 $(OH)_2D_3$ is absent, a complex of FLAG-VDR and CDP is not formed and FLAG-VDR is immunoprecipitated.

Example 10

Binding of CDP to HOS Cell-Specific VDR

Figure 10:
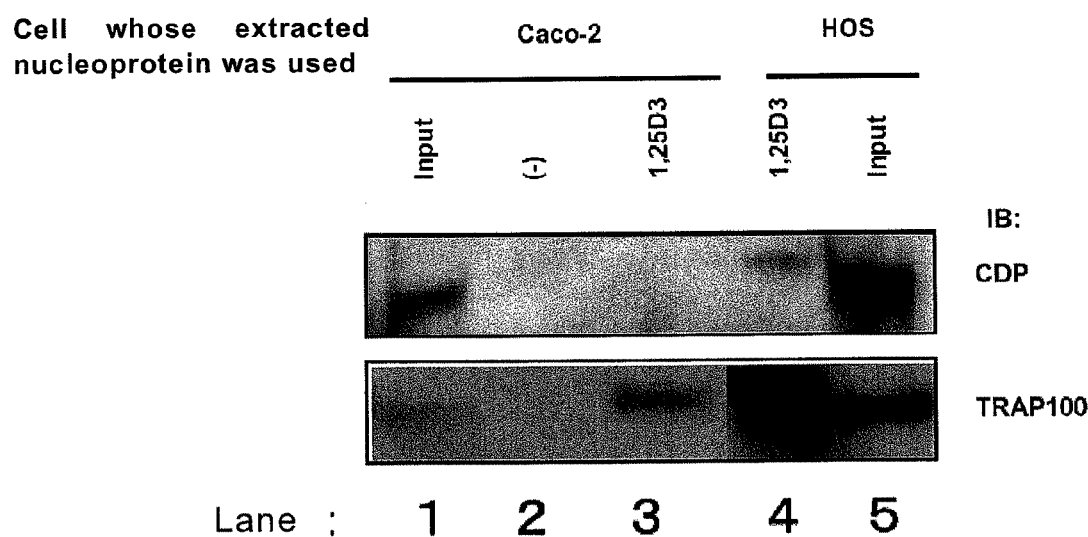
FIG. 10 is a western blot image showing presence or absence of binding between CDP and FLAG-VDR when HOS cells containing both CDP and FLAG-VDR or only CDP are cultured both in the presence and the absence of 1,25 (OH)$_2$D$_3$. The images show, from the top row down, the detection obtained by using anti-CDP antibody and anti-TRAP 100 antibody.

In the same manner as Examples 2 and 3, a nuclear protein extract was obtained from Caco-2 cells in order to test whether or not CDP and VDR bind in a ligand-dependent manner. The results are shown in FIG. 10. The results were examined by using a nuclear protein extract from HOS cells for comparison. "Input" shows the lane in which the nuclear protein extract is used without modification in SDS-PAGE before mixing with GST-VDR resin. The nuclear protein extract derived from Caco-2 was mixed overnight at 4° C. with GST-VDR in the presence and the absence of 1,25 $(OH)_2$ $D_3$ and then the resin was washed in buffer-D and eluted with reduced glutathione and subjected to SDS-PAGE. CDP and TRAP100 were detected using western blotting. However, proteins originating from HOS cells were mixed overnight at 4° C. with GST-VDR in the presence of 1,25 $(OH)_2D_3$ ($10^{-6}$ M). The results of western blotting are shown in FIG. 10. Lane 1 shows that CDP is also expressed in Caco-2 cells. Lanes 2 and 3 show that, although the known factor TRAP100 which binds and forms complexes with VDR in the presence of 1,25 $(OH)_2D_3$ is bonded to GST-VDR, CDP is not bonded to GST-VDR. On the other hand, in Lane 4 in which a nuclear protein extract from HOS cells was used, CDP bind to GST-VDR in the presence of a ligand. The above results show that CDP binds to VDR in an osteoblast-specific manner in the presence of 1,25 $(OH)_2D_3$.

Example 11

Isolation of a CDP-VDR Complex from a DRIP Complex

Figure 11:
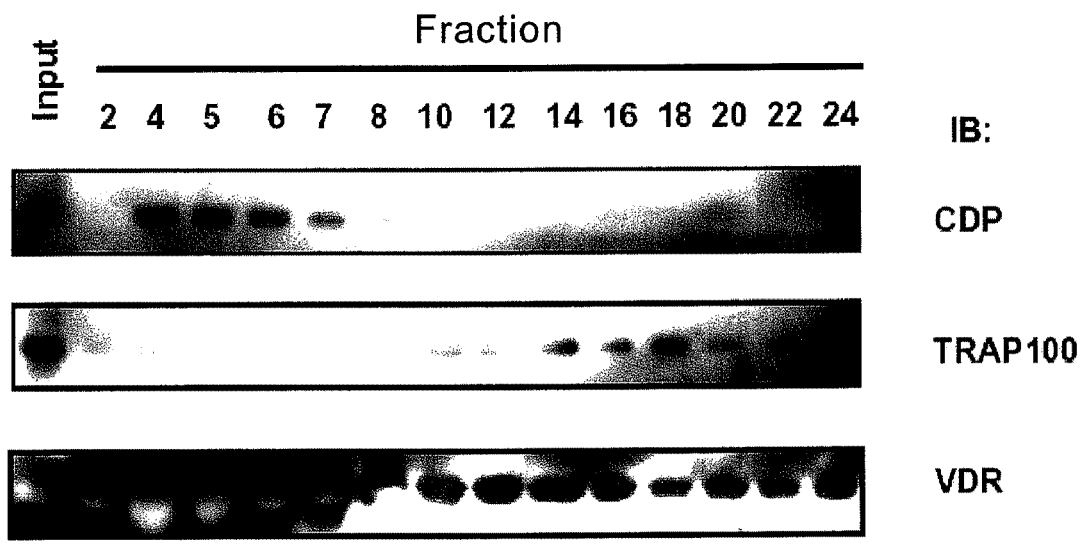
FIG. 11 shows a fraction of a protein and a protein complex binding with GST-VDR in the presence of 1,25 (OH)$_2$D$_3$. The images show, from the top row down, the detection obtained by using anti-CDP antibody, anti-TRAP100 antibody and anti-VDR antibody.

In order to examine, by using a nuclear protein extract from HOS cells, the respective molecular weights of a complex of GST-VDR and CDP formed in the presence of 1,25 $(OH)_2D_3$ and the known DRIP complex which is a VDR protein complex, samples containing a complex with GST-VDR were size-fractionated using a method of glycerol density gradient centrifugation. Firstly, in the same manner as Examples 2 and 3, a complex formed in the presence of 1,25 $(OH)_2D_3$ ($10^{-6}$ M) was eluted using reduced glutathione and layered into the uppermost section of a centrifugation tube (Hitachi Koki, Product Name 13PA Tube) holding 10 mL of a buffer having a concentration gradient of glycerol in a composition of buffer-D of 20-50%. Centrifugation was performed using an RPS-40T480 rotor (Hitachi Koki) at 38,000 rotations, 4° C. for 16 hours (Hitachi Koki, CP70G or CP100MX). After separation by centrifuging, 300 microliter portions were recovered from the upper layer and fractionated. Equal amounts of 20% trichloroacetic acid/acetone were added to respective solutions, and the resultant mixtures were allowed to stand in an ice bath for 10 minutes. The protein was precipitated by centrifuging for 30 minutes at 4° C. and at about 15,000×g. The supernatant was removed and after washing the precipitate in iced ethanol, the mixture was dried and dissolved in SDS sample buffer. This solution was subjected to SDS-PAGE and as described above, western blotting was used to detect CDP, TRAP100 and VDR proteins. The primary antibody for VDR detection was anti-VDR(C-20) rabbit IgG (Santa Cruz Biotechnology, Product No. sc-1008). The secondary antibody was anti-rabbit IgG HRP (Amersham Bioscience, Product No. NA934A). ECL Plus (GE Healthcare Bioscience, Product No. RPN2132) as a reagent was used in the detection. The results are shown in FIG. 11. "Input" shows the reduced glutathione eluate of a protein binding to GST-VDR in the presence of 1,25 $(OH)_2D_3$ prior to fractionation. The fractions with lower numbers show fractions having lower glycerol density, and protein complexes having lower molecular weights are fractionated than the fractions (lower layer) with large numbers. Based on a preliminary test using 20-50% glycerol density gradient centrifugation, it has been shown that 150 kDa protein is fractionated near to the fifth fraction and 760 kDa protein is fractionated near to the eighth fraction. The results are shown in FIG. 11. The result that TRAP100 which is a component of a DRIP complex which is known to be ligand-dependent VDR complex is detected from the tenth fraction to the twenty second fraction suggests at least that a complex of the level of 1 MDa is formed. The actual DRIP complex is known to form a complex with a size of about 1 MDa. On the other hand, CDP is detected from the fourth fraction to the eighth fraction. CDP appearing in the fourth and fifth fractions wherein proteins having a molecular weight of approximately 150-200 kDa are expected to be fractionated is considered not to be in the form of any complex. However, the CDP fractionated in the sixth to eighth fractions is suggested to form a complex of approximately 300-760 kDa. Since VDR was detected in all fractions, it can be seen that VDR is present in CDP and DRIP complexes. These results show that complexes formed from CDP and VDR are novel protein complexes different from the DRIP complexes.

Figure 12:
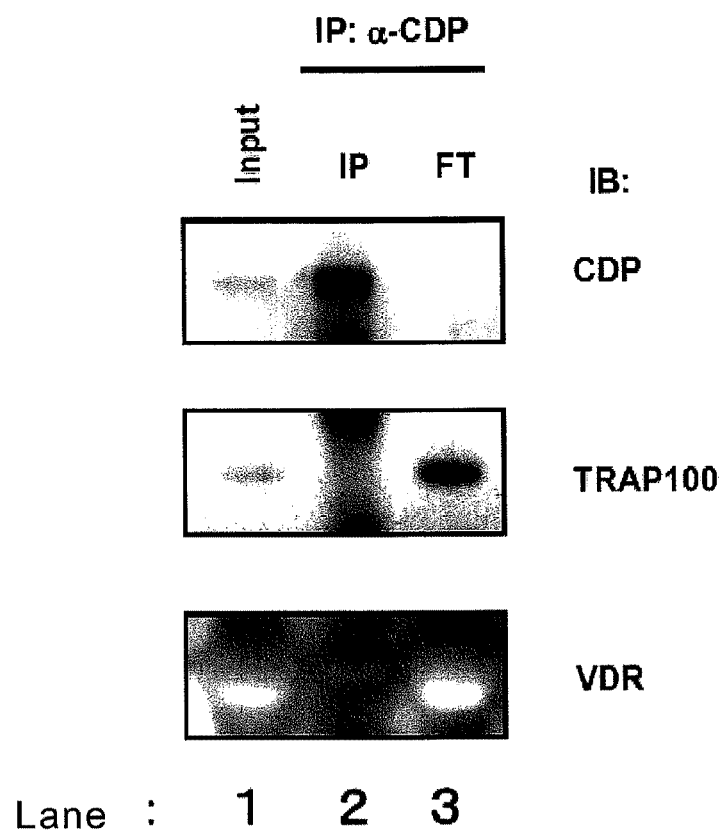
FIG. 12 shows identification of complex of CDP and VDR separately from a DRIP complex by immuno-precipitation of a protein binding with GST-VDR in the presence of 1,25 (OH)$_2$D$_3$ using an anti-CDP antibody. The images show, from the top row down, the detection obtained by using anti-CDP antibody, anti-TRAP100 antibody and anti-VDR antibody.

Anti-CDP goat IgG (C-20) (Santa Cruz Biotechnology, Product No. sc-6327) was added to a 400 microliter of reduced glutathione eluate of a protein complex binding to VDR in the presence of a ligand bound to GST-VDR resin prior to application of glycerol density gradient centrifugation and the resultant solution was mixed for two hours at 4° C. Protein G Sepharose 4 Fast Flow (hereafter Protein G resin) (GE Healthcare Bioscience, Product No. 17-0618-01) was added to the solution, followed by mixing further two hours at 4° C. Thereafter, the Protein G resin was collected by centrifugation and recovered by flow-through. The Protein G resin was washed four times in buffer D, SDS sample buffer added and the protein bound to the Protein G resin was subjected to SDS-PAGE and western blotting. SDS sample buffer was also added to the flow-through part containing proteins not binding to CDP and subjected to western blotting. The results are shown in FIG. 12. "Input" in Lane 1 of the figure shows the reduced glutathione eluate sample of the protein binding to GST-VDR in the presence of 1,25 $(OH)_2D_3$ prior to addition of the anti-CDP antibody. In Lane 2, a protein that is immunoprecipitated using the anti-CDP antibody was run. CDP was detected while TRAP100 was not. On the other hand, the flow-through (FT) part in Lane 3 did not show the presence of CDP but TRAP100 was detected. Furthermore, VDR was detected across Lanes 1 to 3. These results show that CDP-VDR complexes are complexes that are different from known DRIP complexes containing TRAP 100.

Example 12

Action of CDP in Osteoblast Differentiation Systems of Human Cells from Periosteum An adenovirus for over expression of CDP in mammals was prepared in accordance with Adeno-X Expression System 2 [Clontech Laboratories Inc. (USA)]. In addition, an adenovirus not expressing CDP was prepared for comparison (Ad-Mock).

Figure 13:
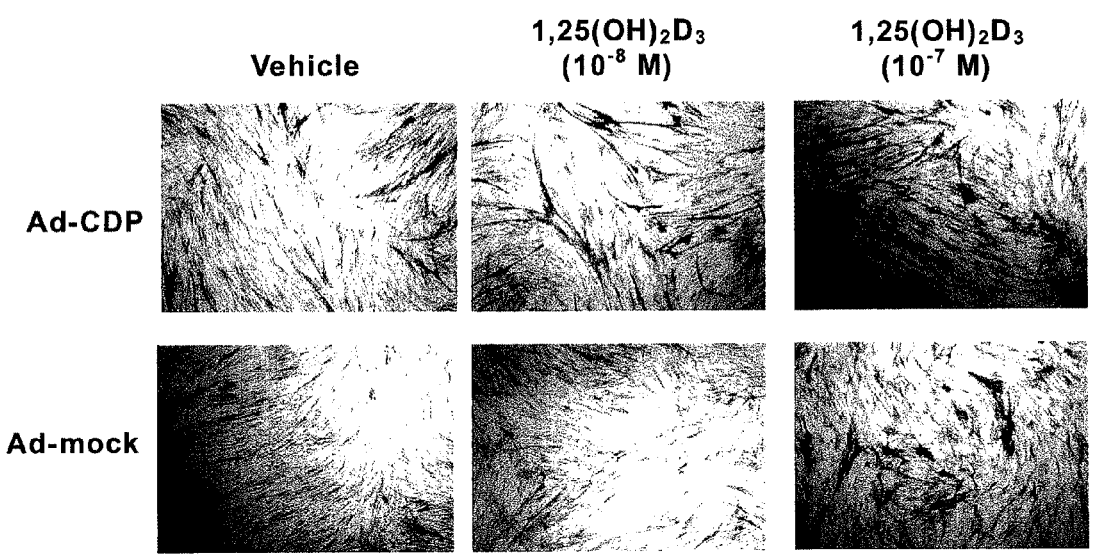
FIG. 13 shows osteoblast-like cells (SaM-1) stained with alkali phosphatase and stimulated by 1,25 (OH)$_2$D$_3$ at various concentrations. The upper row shows the group (Ad-CDP) displaying over-expression of CDP and the lower group (Ad-mock) not displaying over-expression of CDP and infected with an unmodified adenovirus.

SaM-1 cells were cultured in a medium (proliferation medium) Minimum Essential Medium Alpha Medium (Invitrogen, Product No. 12571-071), 10% fetal bovine serum and 0.1 mg/mL kanamycin. The cells were used to inoculate a 24 well multi-well plate and cultured. When the cells reached 80% confluence, the medium was exchanged for a proliferation medium containing the virus, cultured overnight in order to infect the cells with the virus. Then the medium was exchange for a proliferation medium not containing a virus. The results are shown in a figure, where the plate infected with a virus overexpressing CDP is labeled (Ad-CDP) and the plate infected with a virus not overexpressing CDP is labeled Ad-mock (FIG. 13). Furthermore, after culturing overnight, the medium was exchanged for a differentiation medium containing Vehicle or 1,25 $(OH)_2D_3$ ($10^{-8}$–$10^{-7}$ M) (medium prepared by adding 2 mM α-glycerophosphate (Tokyo Chemical Industry, Product No. G0096) to the proliferation medium). The medium was exchanged every two days and cultured for seven days. After seven days culturing, alkaline phosphatase staining was performed. Both the Ad-CDP and the Ad-mock groups displayed an increase in the number of alkaline phosphatase-positive cells stained blue by 1,25 $(OH)_2 D_3$ stimulation. Furthermore, the Ad-CDP group displayed a conspicuously higher increase in the number of alkaline phosphatase-positive cells resulting from 1,25 (OH)$_2$ D$_3$ stimulation. These results suggest that the action of 1,25 (OH)$_2$D$_3$ stimulation is increased in the osteoblast differentiation process as a result of over-expression of CDP.

The same example may be applied to other osteoblast-like cells in addition to SaM-1.

INDUSTRIAL APPLICABILITY

According to the present invention, a novel method of screening VDR ligands participating in osteoblast differentiation is provided. For example, the method may be used to select test compounds displaying a strong osteoblast selective activity and allow for the early manufacture of therapeutic agents displaying selective VDR-ligand action to osteoblasts while reducing or eliminating side effects such as increases in blood levels of calcium.

According to the present invention, a novel in vitro method of screening VDR ligands participating in osteoblast differentiation is provided. Since the compounds obtained by the screening method of the present invention display a conspicuously high action with respect to osteoblasts, a novel method is provided in order to screen compounds having strong bone formation effects and low side effects such as hypercalcemia.

The invention claimed is:

1. A method of screening a compound that increases the transcriptional activity by a complex of a vitamin D receptor and CCAAT Displacement Protein (CDP), comprising the step of detecting the increase in the transcriptional activity by the complex of a vitamin D receptor and CDP in the presence of a test compound.

2. The method of screening according to claim 1, wherein the compound is a compound having affinity for at least one of a vitamin D receptor and CDP.

3. The method of screening according to claim 1 or 2, wherein the step of detecting the increase in the transcriptional activity by a complex of a vitamin D receptor and CDP comprises detecting a further increase in the vitamin D receptor-mediated transcriptional activity by over-expression of CDP.

4. The method of screening according to claim 1 or 2, wherein the step of detecting the increase in the transcriptional activity by a complex of a vitamin D receptor and CDP comprises detecting a further increase in the CDP-mediated transcriptional activity by over-expression of the vitamin D receptor.

5. The method of screening according to claim 1 or 2, wherein the increase in the transcriptional activity by a complex of a vitamin D receptor and CDP is detected in a cell producing or expressing both the vitamin D receptor and CDP.

6. The method of screening according to claim 5, wherein the cell producing or expressing both the vitamin D receptor and CDP is a cell expressing at least one osteoblast marker selected from the group consisting of alkali phosphatase, osteocalcin, bone sialoprotein and Runx2.

7. The method of screening according to claim 5, wherein the cell producing or expressing both the vitamin D receptor and CDP is a cell into which at least one of a vitamin D receptor gene and a CDP gene is introduced.

8. The method of screening according to claim 1 or 2, wherein the increase in the transcriptional activity by the complex of the vitamin D receptor and CDP is measured using a reporter gene assay system.

9. The method of screening according to claim 1 or 2, wherein the increase in the transcriptional activity by the complex of the vitamin D receptor and CDP is measured using expression of a vitamin D receptor target gene or a differentiation marker gene for an osteoblast as an indicator.

10. The method of screening according to claim 9, wherein the vitamin D receptor target gene is a CYP24 gene and the osteoblast differentiation marker is selected from the osteocalcin gene and the alkaline phosphatase gene.

11. The method of screening according to claim 1 or 2, wherein the test compound is a vitamin D derivative.

12. The method of screening according to claim 1 or 2, wherein the test compound is a compound inducing differentiation into osteoblast.

13. The method of screening according to claim 1 or 2, wherein the compound is a compound displaying bone mass increasing action in animals.

14. A kit for performing the screening method according to claim 1 or 2, comprising: (a) a vector for evaluating an increase in the vitamin D receptor-mediated transcriptional activity, the vector comprising a DNA sequence to which a vitamin D receptor binds and a reporter gene; (b) a vector for evaluating an increase in the CDP mediated transcriptional activity, the vector comprising a DNA sequence to which CDP binds and a reporter gene; and (c) a reagent for detecting a product of the reporter gene.

15. A kit for performing the screening method according to claim 1 or 2, comprising: (a) a vector for evaluating the increase in the transcriptional activity mediated by a complex of the vitamin D receptor and CDP, the vector comprising a DNA sequence to which a vitamin D receptor binds, a DNA sequence to which CDP binds and a reporter gene; and (b) a reagent for detecting a product of the reporter gene.

* * * * *